United States Patent [19]

Sumino et al.

[11] Patent Number: 5,856,521

[45] Date of Patent: Jan. 5, 1999

[54] ACRYLIC OR METHACRYLIC ACID DERIVATIVES AND POLYMERS OBTAINED THEREFROM

[75] Inventors: Motoshige Sumino; Kazuhito Fukasawa, both of Kawagoe, Japan

[73] Assignee: Wako Pure Chemical Industries, Ltd., Osaka, Japan

[21] Appl. No.: 66,900

[22] Filed: Apr. 28, 1998

[30] Foreign Application Priority Data

Apr. 30, 1997 [JP] Japan .................................. 9-126391

[51] Int. Cl.⁶ ..................... C07D 305/06; C07D 331/04; C07C 255/03; C08F 20/10
[52] U.S. Cl. ..................... 549/214; 549/88; 558/443; 526/329.4; 526/341; 560/128; 560/187
[58] Field of Search ..................... 558/443; 526/329.4, 526/341; 549/88, 214; 560/128, 187

[56] References Cited

U.S. PATENT DOCUMENTS 3,728,322 4/1973 Freyermuth et al. .................. 260/91.3
5,059,698 10/1991 Schulthess et al. ..................... 549/375

OTHER PUBLICATIONS

Derwent WPI, Abstract of JP 7–199467 (Aug. 4, 1995).
Derwent WPI, Abstract of JP 8–82925 (Mar. 26, 1996).
Derwent WPI, Abstract of JP 7–234511 (Sep. 5, 1995).

Primary Examiner—Johann Richter
Assistant Examiner—Ebenezer Sackey
Attorney, Agent, or Firm—Armstrong, Westerman, Hattori, McLeland & Naughton

[57] ABSTRACT

A monomer of the formula:

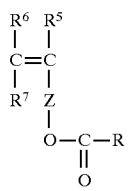

wherein R5, R6 and R7 are independently hydrogen, alkyl, cyano, alkyloxycarbonyl or carbamoyl; Z is a spacer or a direct link; and R is hydroxyalkyl having a protected terminal hydroxy, can produce a polymer useful for producting a resist composition.

14 Claims, No Drawings

ACRYLIC OR METHACRYLIC ACID DERIVATIVES AND POLYMERS OBTAINED THEREFROM

BACKGROUND OF THE INVENTION

The present invention relates to novel polymers useful, for example, for preparation of resist compositions used for production of semiconductor devices, etc., and novel acrylic or methacrylic acid derivatives usable as materials for said polymers.

Novolak resins and polymers comprising acrylic acid units or methacrylic acid units have been known as alkali-soluble resins. of these, various polymers have been put to practical use as materials for photolithography or materials for electronics industry, such as resist materials. Particularly in the lithography field, g-line light sources (wavelength 436 nm), i-line light sources (wavelength 365 nm) for ultraviolet light, and recently excimer lasers (KrF excimer laser: wavelength 248 nm, ArF excimer laser: wavelength 193 nm) are used as a light source for exposure. As the base polymer of a resist material suitable for each of these light sources, novolak resins are mainly used in resists for i-line or g-line light and phenolic resins are mainly used in resists for KrF excimer laser beams. Both the novolak resins and the phenolic resins have phenolic hydroxyl groups ($pk_a$: about 12) as functional groups which permit development with an alkali developing solution.

On the other hand, acrylic acid derivative or methacrylic acid derivative resins are leading base polymers used in resist materials for ArF excimer laser beams which are under development (for example, JP-A 7-199467, JP-A 8-82925, JP-A 7-234511, etc.).

The reason is that conventional resins having aromatic rings have a low transparency in the deep ultraviolet region and are quite opaque at 193 nm, the wavelength of ArF excimer laser beams.

The resist materials obtained by using the acrylic or methacrylic resin as the base polymer, however, have a high acidity ($pk_a$: about 5) because of their carboxylic acid groups as soluble groups and hence have a much rapider dissolution rate in alkali development than do the conventional polymers having phenolic hydroxyl groups as soluble groups. Therefore, they are disadvantageous in that when a 2.38% aqueous tetramethylammonium hydroxide (TMAH) solution, a conventional alkali developing solution is used without dilution, film peeling or dissolution of non-exposed portion occurs in the formation of a fine pattern, so that no satisfactory pattern can be obtained.

Moreover, the above-mentioned 2.38% TMAH is a leading alkali developing solution employed at present in an actual production line of semiconductor devices, so that it is very difficult to use a diluted developing solution in a production line in which there is used a combination of resist materials of different generations, such as a combination of a resist for i-line light and a resist for KrF excimer laser beams or a combination of a resist for KrF excimer laser beams and a resist for ArF excimer laser beams.

SUMMARY OF THE INVENTION

The present invention was made in view of such conditions and is intended to provide a novel polymer which has high transmittance to deep ultraviolet light of a wavelength of 220 nm or less, in particular, ArF excimer laser beams, etc., and gives a resist film excellent in resistance to etching, etc. when used for preparing a resist composition; and a novel acrylic or methacrylic acid derivative usable as a starting monomer for said polymer.

The present invention provides a monomer represented by the formula:

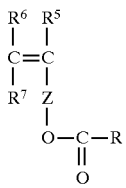

[1]

wherein $R^5$, $R^6$ and $R^7$ are independently a hydrogen atom, an alkyl group, a cyano group, an alkyloxycarbonyl group or a carbamoyl group; Z is a spacer or a direct link; and R is a hydroxyalkyl group having a protected terminal hydroxyl group.

The present invention also provides a polymer comprising as constituent units monomer units represented by the formula:

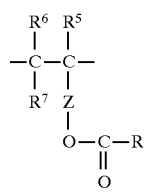

[1a]

wherein $R^5$, $R^6$, $R^7$, Z and R are as defined above.

DESCRIPTION OF THE PREFERRED EMBODIMENTS

The present inventors earnestly investigated in order to achieve the above object, and consequently found a novel polymer comprising as constituent units monomer units of the formula [1a] derived from the monomer of the following formula [1], which has a high light transmittance in a wavelength region or 220 nm or less, and gives a resist film excellent in resistance to etching when used as a resist material. Thus, the present invention has been accomplished:

Monomer: a monomer represented by

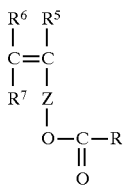

[1]

wherein $R^5$, $R^6$ and $R^7$ are independently a hydrogen atom, an alkyl group, a cyano group, an alkyloxycarbonyl group or a carbamoyl group; Z is a spacer or a direct link; and R is a hydroxyalkyl group having a protected terminal hydroxyl group.

Polymer: a polymer comprising as constituent units monomer units represented by

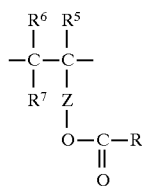

wherein $R^5$, $R^6$, $R^7$, Z and R are as defined above.

In the above formulae [1] and [1a], the alkyl group represented by each of $R^5$, $R^6$ and $R^7$ may be linear or branched and includes, for example, alkyl groups having 1 to 12 carbon atoms, preferably 1 to 8 carbon atoms. Specific examples thereof are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, etc.

The alkyloxycarbonyl group represented by each of $R^5$, $R^6$ and $R^7$ may be linear, branched or cyclic and includes, for example, alkyloxycarbonyl groups having 2 to 19 carbon atoms. The cyclic alkyloxycarbonyl groups may be monocyclic or polycyclic and include, for example, alicyclic alkyloxycarbonyl groups having 6 to 14 carbon atoms. Specific examples of the alkyloxycarbonyl group are methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, a tert-butyloxycarbonyl group, a 2-ethylhexyloxycarbonyl group, a cyclohexyloxycarbonyl group, a tricyclodecyloxycarbonyl group, a tricycloundecyloxycarbonyl group, a tricyclododecyloxycarbonyl group, a tricyclotetradecyloxycarbonyl group, a tetrahydropyranyloxycarbonyl group, an adamantyloxycarbonyl group, a 2-methyl-2-adamantyloxycarbonyl group, a norbornyloxycarbonyl group, a bicyclo-[3.2.1]octenyloxycarbonyl group, a bicyclo[2.2.2]octyloxycarbonyl group, a menthyloxycarbonyl group, an isobornyloxycarbonyl group, etc.

The spacer represented by Z includes, for example, groups represented by the formula [4]:

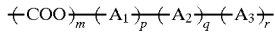

wherein $A_2$ is a divalent hydrocarbon group which may have one or more oxygen atoms; $A_1$ and $A_3$ are independently a lower alkylene group; m is 0 or 1; and p, q and r are independently 0 or 1, provided that q is 1 in the case of m being 1.

In the formula [4], the divalent hydrocarbon group represented by $A_2$ which has no oxygen atom includes, for example, alkylene groups having 1 to 20 carbon atoms, preferably 1 to 10 carbon atoms, divalent aromatic groups, etc. The alkylene groups may be linear, branched or cyclic. Specific examples thereof are a methylene group, an ethylene group, a propylene group, a butylene group, a 2-methylpropylene group, a pentylene group, a 2,2-dimethyl-propylene group, a 2-ethylpropylene group, a hexylene group, a heptylene group, an octylene group, a 2-ethylhexylene group, a nonylene group, a decylene group, a cyclopropylene group, a cyclopentylene group, a cyclohexylene group, an adamantanediyl group, a tricyclo-[5.2.1.0$^{2.6}$]decanediyl group, a norbornanediyl group, a methylnorbornanediyl group, an isobornanediyl group, a decalindiyl group, etc.

The divalent aromatic groups include, for example, an o-phenylene group, a m-phenylene group, a p-phenylene group, a diphenylene group, a p-xylene-α,α'-diyl group, a —$CH_2$—$C_6H_4$— group, etc.

The divalent hydrocarbon group represented by $A_2$ which has one or more oxygen atoms includes those derived from the above-exemplified divalent hydrocarbon groups which contain in the chain one or more oxygen atoms, preferably 1 to 3 oxygen atoms. Specific examples thereof re a methoxyethylethylene group, an ethoxyethylethylene group, a bornyloxyethylethylene group, a norbornyloxyethylthylene group, a menthyloxyethylethylene group, an adamantyloxyethylethylene group, a methoxyethoxyethyl-ethylene group, an ethoxyethoxyethylethylene group, a bornyloxyethoxyethylethylene group, a menthyloxyethoxy-ethylethylene group, a —$CH_2$—O—$CH_2$— group, a —$CH_2CH_2$—O—$CH_2$— group, a —$CH_2CH_2$—O—$CH_2CH_2$— group, a —$CH_2CH_2$—O—$CH_2CH_2$—O—$CH_2CH_2$— group, a —$CH_2$—O—$C_6H_4$— group, etc.

The lower alkylene group represented by each of $A_1$ and $A_3$ may be linear or branched and includes, for example, alkylene groups having 1 to 6 carbon atoms. Specific examples thereof are a methylene group, an ethylene group, propylene group, a butylene group, a 2-methyl-propylene group, a pentylene group, a 2,2-dimethylpropylene group, a 2-ethylpropylene group, a hexylene group, etc.

The hydroxyalkyl group with a protected terminal hydroxyl group represented by R may be linear, branched or cyclic and may have a double bond. It includes, for example, groups represented by the following formula [2] or [3]:

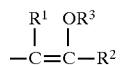

wherein $R^1$ and $R^2$ are independently a hydrogen atom, a substituted or unsubstituted alkyl group or an alicyclic hydrocarbon group, and $R^1$ and $R^2$ may form together an aliphatic ring; and $R^3$ is an alkyl group, an alkenyl group, a hydroxyalkyl group, an alkyloxycarbonyl group or an alkylsilyl group.

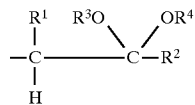

wherein $R^4$ is an alkyl group; and $R^1$, $R^2$ and $R^3$ are as defined above, and R3 and $R^4$ may form together an aliphatic ring.

In the formulae [2] and [3], the unsubstituted alkyl group represented by each of $R^1$ and $R^2$ may be linear, branched or cyclic and includes, for example, alkyl groups having 1 to 12 carbon atoms, preferably 1 to 8 carbon atoms. Specific examples thereof are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, a cyclopropyl group, a cyclopentyl group, a cyclohexyl group, a 2-cyclohexylethyl group, etc.

As the substituted alkyl group represented by each of $R^1$ and $R^2$, there can be exemplified by those obtained by substituting each of usually 1 to 17, preferably 1 to 10, of the hydrogen atoms of the above-exemplified alkyl group by, for example, a cyano group, a hydroxyl group, a halogen atom (e.g. fluorine, chlorine, bromine or iodine), or a lower alkoxy group having 1 to 6 carbon atoms (e.g. methoxy group, ethoxy group, propoxy group, 2-propoxy group, butoxy group, tert-butoxy group, pentyloxy group or hexyloxy group). Specific examples of the substituted alkyl group are cyano-containing alkyl groups such as cyanomethyl, cyanoethyl, cyanopropyl, cyanobutyl, cyanopentyl, cyanohexyl, and cyanoheptyl; hydroxyalkyl groups such as hydroxymethyl, hydroxyethyl, hydroxypropyl, hydroxybutyl, hydroxypentyl, hydroxyhexyl, hydroxyheptyl, and hydroxyoctyl; haloalkyl groups such as chloromethyl, bromomethyl, trifluoromethyl, 2-chloroethyl, 3-chloropropyl, 3-bromopropyl, 3,3,3-trifluoropropyl, and perfluorooctyl; and alkoxyalkyl groups such as methoxymethyl, methoxyethyl, ethoxymethyl, ethoxyethyl, propoxymethyl, 2-propoxymethyl, propoxyethyl, butoxymethyl, and tert-butoxymethyl.

The alicyclic hydrocarbon group represented by each of $R^1$ and $R^2$ includes, for example, alicyclic hydrocarbon groups having 3 to 30 carbon atoms, preferably 5 to 12 carbon atoms. Specific examples thereof are a tricyclo [5.2.1.0$^{2.6}$]decanyl group, a dicyclopentenyl group, an adamantyl group, a norbornyl group, an isobornyl group, a 2-methyl-2-adamantyl group, a menthyl group, etc.

The aliphatic ring formed together by $R^1$ and $R^2$ may be monocyclic or polycyclic and includes, for example, rings composed of an alkylene chain having 3 to 10 carbon toms. Specific examples of the ring are a 2-norbornane ing, a cyclopentane ring, a cyclohexane ring, a cycloctane ring, a cyclodecane ring, a 2-norbornene ring, a cyclopentene ring, a cyclohexene ring, a cyclooctene ring, a cyclodecene ring, etc.

The alkyl group represented by $R^3$ may be linear or branched and includes, for example, alkyl groups having 1 to 12 carbon atoms, preferably 1 to 8 carbon atoms. Specific examples thereof are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, etc.

The alkenyl group represented by $R^3$ may be linear or branched and includes, for example, alkenyl groups having 2 to 12 carbon atoms, preferably 2 to 8 carbon atoms. Specific examples thereof are an ethenyl group, a propenyl group, an isopropenyl group, a butenyl group, an isobutenyl group, a pentenyl group, an isopentenyl group, a hexenyl group, an isohexenyl group, a heptenyl group, an octenyl group, etc.

The hydroxyalkyl group represented by $R^3$ may be linear or branched and includes, for example, hydroxyalkyl groups having 1 to 12 carbon atoms, preferably 2 to 8 carbon atoms. Specific examples thereof are a hydroxyethyl group, a hydroxypropyl group, a hydroxybutyl group, a ydroxypentyl group, a hydroxyhexyl group, a hydroxyheptyl group, a hydroxyoctyl group, etc.

The alkyloxycarbonyl group represented by $R^3$ may be linear, branched or cyclic and includes, for example, alkyloxycarbonyl groups having 2 to 19 carbon atoms. Specific examples thereof are an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, a tert-butyloxycarbonyl group, a 2-ethylhexyloxycarbonyl group, a cyclohexyloxycarbonyl group, etc.

The alkyl group of the alkylsilyl group represented by $R^3$ may be linear or branched and includes, for example, alkyl groups having 1 to 6 carbon atoms. Specific examples thereof are a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, etc. The alkylsilyl group includes, for example, those having 1 to 18 carbon atoms, preferably 1 to 9 carbon atoms. Specific examples thereof are trialkylsilyl groups such as trimethylsilyl, triethylsilyl, tri-n-propylsilyl, triisopropylsilyl, tri-n-butylsilyl, tripentylsilyl, tri-n-hexylsilyl, and tert-butyldimethylsilyl.

In the formula [3], the alkyl group represented by $R^4$ may be linear or branched and includes, for example, alkyl groups having 1 to 12 carbon atoms, preferably 1 to 8 carbon atoms. Specific examples thereof are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, etc.

The aliphatic ring formed together by $R^3$ and $R^4$ may be monocyclic or polycyclic and includes rings composed of an alkylene chain having 2 to 10 carbon atoms, preferably 2 to 4 carbon atoms. The alkylene chain may be linear or branched and may have a hydroxyl group. In addition, the alkylene chain may have an —O— group and/or a double bond at an arbitrary position in the chain. Specific examples of the alkylene chain are an ethylene group, a propylene group, an isopropylene group, an isopropylidene group, a butylene group, a 2-methylpropylene group, a pentylene group, a 2,2-dimethylpropylene group, a 2-ethylpropylene group, a hexylene group, a 2-butyl-2-ethylpropylene group, an ethenylene group, a propenylene group, a butenylene group, a vinylidene group, a —CH$_2$C(=CH$_2$)CH$_2$— group, a 1-hydroxyethylene group, a 2-hydroxypropylene group, a 2-hydroxybutylene group, a 2-hydroxypentylene group, a 3-hydroxypentylene group, a 2-hydroxyhexylene group, a 3-hydroxyhexylene group, a —CH$_2$—O—CH$_2$— group, a —CH$_2$CH$_2$—O—CH$_2$— group, a —CH$_2$CH$_2$—O—CH$_2$CH$_2$— group, etc.

The monomer unit of the above formula [1a] contained in the polymer of the present invention is derived from the monomer of the above formula [1]. This monomer includes, for example, those represented by the following formulae [1]-1, [1]-2, [1]-3 and [1]-4:

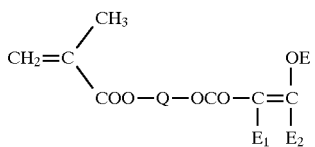

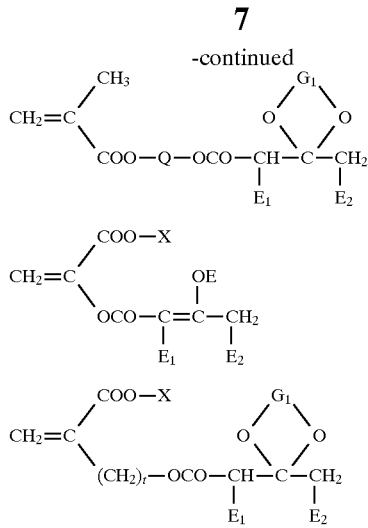

[1]-2

[1]-3

[1]-4 wherein Q is a divalent hydrocarbon group which may have one or more oxygen atoms; E is a lower alkyl group; X is an alkyl group; $G_1$ is a lower alkylene group; t is an integer of 0 to 6; and $E_1$ and $E_2$ are independently a hydrogen atom, and $E_1$ and $E_2$ may form together an aliphatic ring.

In the above formulae [1]-1 and [1]-2, when the divalent hydrocarbon group which may have one or more oxygen atoms and is represented by Q has no oxygen atom, the divalent hydrocarbon group includes, for example, alkylene groups having 1 to 20 carbon atoms, preferably 1 to 10 carbon atoms, divalent aromatic groups, etc.

The alkylene groups may be linear, branched or cyclic. Specific examples thereof are a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, a cyclopropylene group, a cyclopentylene group, a cyclohexylene group, an adamantanediyl group, a tricyclo-[5.2.1.0$^{2.6}$]decanediyl group, a norbornanediyl group, a methylnorbornanediyl group, an isobornanediyl group, a decalindiyl group, etc.

The divalent aromatic groups include, for example, an o-phenylene group, a m-phenylene group, a p-phenylene group, a diphenylene group, a p-xylene-α,α'-diyl group, a —CH$_2$—C$_6$H$_4$— group, etc.

The divalent hydrocarbon group represented by Q which has one or more oxygen atoms includes those derived from the above-exemplified alkylene groups which contain 1 to 3 —O— groups in the chain. Specific examples thereof are —CH$_2$—O—CH$_2$—, —CH$_2$CH$_2$—O—CH$_2$—, —CH$_2$—O—CH$_2$CH$_2$—, —CH$_2$CH$_2$—O— CH$_2$CH$_2$—, —CH$_2$—O—CH$_2$—O—CH$_2$—, —CH$_2$CH$_2$—O—CH$_2$—O— CH$_2$CH$_2$—, —CH$_2$—O—CH$_2$—O—CH$_2$—O—CH$_2$—, —CH$_2$CH$_2$—O—CH$_2$—O—CH$_2$CH$_2$—O—CH$_2$CH$_2$—, —CH$_2$—O—CH(CH$_2$CH$_3$)—CH$_2$—, —CH$_2$CH$_2$—O— CH(CH$_3$)—O—CH$_2$—,

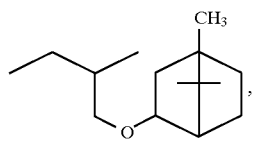

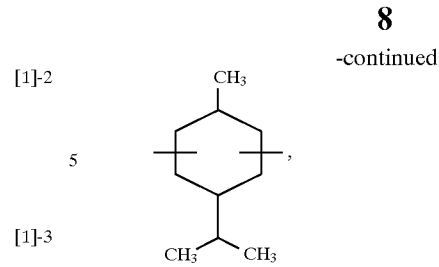

In the above formulae [1]-1 and [1]-3, the lower alkyl group represented by E may be linear or branched and includes, for example, alkyl groups having 1 to 6 carbon atoms. Specific examples thereof are a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, etc.

In the above formulae [1]-3 and (11-4, the alkyl group represented by X may be linear, branched or cyclic and includes, for example, alkyl groups having 1 to 20 carbon atoms, preferably 1 to 15 carbon atoms. The cyclic alkyl group may be monocyclic or polycyclic. Specific examples of the alkyl group are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, a nonyl group, a decyl group, an undecyl group, a dodecyl group, a hexadecyl group, an octadecyl group, a nonadecyl group, an icosyl group, a cyclopropyl group, a cyclopentyl group, a cyclohexyl group, a 2-cyclohexylethyl group, a norbornyl group, an isobornyl group, an adamantyl group, a 2-methyl-2-adamantyl group, a tetrahydropyranyl group, a tricycloundecyl group, a tricyclodecyl group, a tricyclododecyl group, a tricyclotetradecyl group, a menthyl group, a bicyclo[3.2.1]octyl group, a bicyclo-[2.2.2]octyl group, etc.

In the above formulae [1]-2 and [1]-4, the lower alkylene group represented by $G_1$ may be linear or branched and includes, for example, alkylene groups having 1 to 6 carbon atoms. Specific examples thereof are a methylene group, an ethylene group, a propylene group, a butylene group, a 2-methylpropylene group, a pentylene group, a 2,2-dimethylpropylene group, a 2-ethylpropylene group, a hexylene group, etc.

In the above formulae [1]-1 to [1]-4, the aliphatic ring formed together by $E_1$ and $E_2$ may be monocyclic or polycyclic and includes rings formed of an alkylene chain having 2 to 10 carbon atoms, preferably 2 to 4 carbon atoms. The alkylene chain may be linear or branched and may have a double bond. Specific examples of the alkylene chain are an ethylene group, a propylene group, an isopropylene group, an isopropylidene group, a butylene group, a 2-methylpropylene group, a pentylene group, a 2,2-dimethylpropylene group, a 2-ethylpropylene group, a hexylene group, a 2-butyl-2-ethylpropylene group, an ethenylene group, a propenylene group, a butenylene group, a vinylidene group, a —CH$_2$C(=CH$_2$)CH$_2$— group, etc.

Specific examples of the formula [1]-1 are as follows:
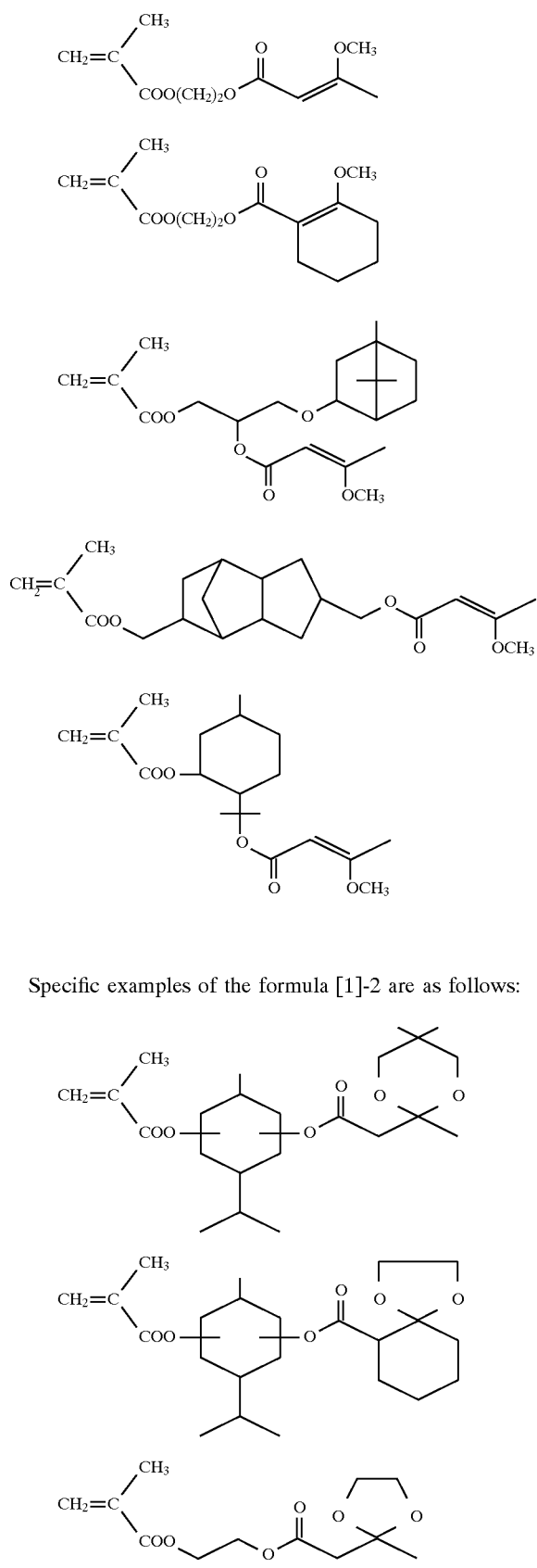
Specific examples of the formula [1]-2 are as follows:
Specific examples of the formula [1]-3 are as follows:
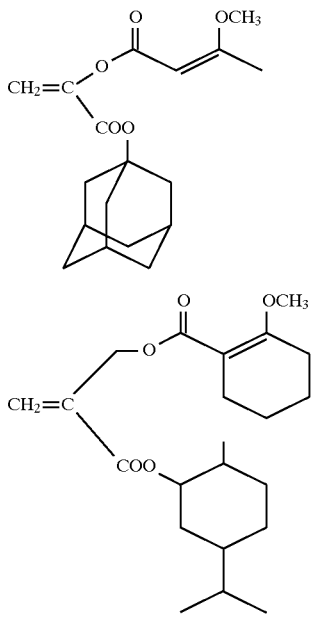
Specific examples of the formula [1]-4 are as follows:
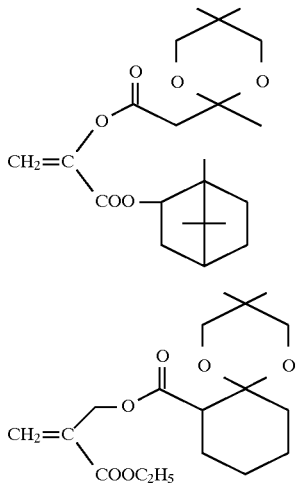
The monomer of the formula [1] of the present invention can be obtained, for example, by reacting a compound of the formula [5]:
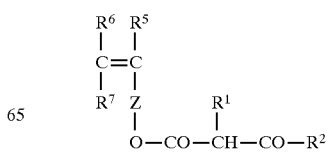
[5]

wherein $R^1$, $R^2$, $R^5$, $R^6$, $R^7$ and Z are as defined above, with an orthocarboxylic ester and optionally an alcohol optionally in a suitable solvent in the presence of an acid catalyst.

The ortho-acid ester includes, for example, trimethyl orthoformate, triethyl orthoformate, trimethyl orthoacetate, triethyl orthoacetate, etc.

Although not particularly limited, the amount of the orthocarboxylic ester used is usually 1 to 30 mols, preferably 3 to 10 mols, per mol of the compound of the formula [5].

The alcohol includes, for example, alcohols having 1 to 12 carbon atoms, preferably 1 to 8 carbon atoms. Specific examples thereof are saturated alcohols such as methanol, ethanol, n-propanol, isopropanol, n-butanol, isobutanol, tert-butanol, sec-butanol, n-pentanol, isopentanol, neopentanol, tert-pentanol, 3,3-dimethylbutanol, 1,1-dimethylbutanol, 1-methylpentanol, n-hexanol, isohexanol, n-heptanol, isoheptanol, n-octanol, isooctanol, and 2-ethylhexanol; and unsaturated alcohols such as allyl alcohol, 3-buten-1-ol, 3-buten-2-ol, crotyl alcohol, 2-methyl-2-propen-1-ol, 2-methyl-3-buten-1-ol, 4-penten-1-ol, 4-penten-2-ol, 3-penten-2-ol, 1-hexen-3-ol, 3-hexen-1-ol, 3-methyl-1-penten-3-ol, 1-hepten-3-ol, 1-octen-3-ol, and 6-methyl-5-hepten-2-ol.

Although not particularly limited, the amount of the alcohol used is usually 1 to 30 mols, preferably 1 to 10 mols, per mol of the compound of the formula [5].

The acid catalyst includes, for example, organic acids or salts thereof such as camphorsulfonic acid, p-toluenesulfonic acid, pyridinium p-toluenesulfonate, oxalic acid, and pyridinium chloride; inorganic acids such as hydrochloric acid, sulfuric acid, and nitric acid; and Lewis acids such as aluminum chloride, and boron trifluoride-diethyl ether complex ($BF_3.Et_2O$).

Although not particularly limited, the amount of the acid catalyst used is usually 0.1 to 20 mol %, preferably 1 to 10 mol %, based on the amount of the compound of the formula [5].

The solvent for reaction used if necessary includes, for example, hydrocarbons such as toluene, xylene, benzene, cyclohexane, n-hexane, and n-octane; halogenated hydrocarbons such as methylene chloride, dichloroethane, and trichloroethylene; esters such as methyl acetate, ethyl acetate, n-butyl acetate, and methyl propionate; alcohols such as methanol, ethanol, n-propanol, isopropanol, n-butanol, isobutanol, and tert-butanol; ethers such as dimethyl ether, diethyl ether, diisopropyl ether, dimethoxyethane, tetrahydrofuran, and dioxane; N-methylpyrrolidone; N,N-dimethylformamide; N,N-dimethyl-acetamide; dimethyl sulfoxide; etc. These may be used singly or in proper combination.

Although not particularly limited, the reaction temperature is usually 0° C. to 150° C., preferably 20° C. to 80° C.

Although the reaction time varies depending on, for example, the kinds and concentrations of the compounds to be reacted, it is usually 0.5 to 10 hours.

The monomer of the formula [1] of the present invention can be obtained also by, for example, reacting a compound of the above formula [5] with a diol optionally in a suitable solvent in the presence of an acid catalyst.

The diol includes, for example, ethylene glycol, propylene glycol, 2,2-dimethylpropanediol, 1,3-butanediol, 1,4-butanediol, diethylene glycol, dipropylene glycol, neopentyl glycol, 1,6-hexanediol, 2,2,4-trimethyl-1,6-hexanediol, triethylene glycol, etc.

Although not particularly limited, the amount of the diol used is usually 1 to 20 mols, preferably 3 to 10 mols, per mol of the compound of the formula [5].

The acid catalyst includes, for example, organic acids or salts thereof such as camphorsulfonic acid, p-toluenesulfonic acid, pyridinium p-toluenesulfonate, oxalic acid, and pyridinium chloride; inorganic acids such as hydrochloric acid, sulfuric acid, and nitric acid; and Lewis acids such as aluminum chloride, and boron trifluoride-diethyl ether complex ($BF_3.Et_2O$).

Although not particularly limited, the amount of the acid catalyst used is usually 0.1 to 20 mol %, preferably 1 to 10 mol %, based on the amount of the compound of the formula [5].

The solvent for reaction used if necessary includes, for example, hydrocarbons such as toluene, xylene, benzene, cyclohexane, n-hexane, and n-octane; halogenated hydrocarbons such as methylene chloride, dichloroethane, and trichloroethylene; esters such as methyl acetate, ethyl acetate, n-butyl acetate, and methyl propionate; ethers such as dimethyl ether, diethyl ether, diisopropyl ether, dimethoxyethane, tetrahydrofuran, and dioxane; N-methylpyrrolidone; N,N-dimethylformamide; N,N-dimethylacetamide; dimethyl sulfoxide; etc. These may be used singly or in proper combination. The solvent for reaction is preferably one which can remove water from the reaction system by forming an azeotropic mixture therewith.

Although not particularly limited, the reaction temperature is usually 0° C. to 150° C., preferably 20° C. to 130° C.

Although the reaction time varies depending on, for example, the kinds and concentrations of the compounds to be reacted, it is usually 0.5 to 48 hours.

In either of the above-mentioned processes, the monomer of the formula [1] obtained may be polymerized as it is without purification and/or isolation (namely, unreacted compound of the formula [5] may be present together with the monomer during the polymerization), or it may be subjected to a subsequent reaction after purification and/or isolation by conventional means such as extraction, recrystallization, etc.

Other operations in the reaction and aftertreatments can be carried out in the same manners as those so far usually used in the same kind of reaction as the above reaction.

As the compound of the formula [5], there may be used either a commercially available one or a product properly prepared by a conventional process.

A monomer of the present invention having an alkylsilyl group can be obtained by reacting the monomer of the present invention obtained by either of the above production processes with an alkylsilyl halide optionally in a suitable solvent in the presence of a basic catalyst.

The alkylsilyl halide includes, for example, chlorotrimethylsilane, chlorotriethylsilane, chlorodimethylethylsilane, chlorotripropylsilane, chlorotriisoropylsilane, chlorotributylsilane, chlorotrihexylsilane, butylchlorodimethylsilane, etc.

Although not particularly limited, the amount of the alkylsilyl halide used is usually 1 to 20 mols, preferably 1 to 5 mols, per mol of the compound of the formula [5].

The basic catalyst includes, for example, organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine; metal hydrides such as sodium hydride; and basic alkali metal compounds such as n-butyllithium, and tert-butyllithium.

Although not particularly limited, the amount of the basic catalyst used is usually 0.1 to 20 mols, preferably 1 to 5 mols, per mol of the compound of the formula [5].

The solvent for reaction used if necessary includes, for example, hydrocarbons such as toluene, xylene, benzene, cyclohexane, n-hexane, n-octane, etc.; halogenated hydrocarbons such as methylene chloride, dichloroethane, and trichloroethylene; esters such as methyl acetate, ethyl acetate, n-butyl acetate, and methyl propionate; ethers such as dimethyl ether, diethyl ether, diisopropyl ether, dimethoxyethane, tetrahydrofuran, and dioxane; N-methylpyrrolidone; N,N-dimethylformamide; N,N-dimethylacetamide; dimethyl sulfoxide; etc. These may be used singly or in proper combination.

Although not particularly limited, the reaction temperature is usually 0° C. to 150° C., preferably 20° C. to 80° C.

Although the reaction time varies depending on the reaction conditions, for example, the kinds and concentrations of the reactants such as the compound of the formula [5], it is usually 0.5 to 48 hours.

The monomer of the formula [1] obtained may be polymerized as it is without purification and/or isolation (namely, unreacted compound of the formula [5] may be present together with the monomer during the polymerization), or it may be subjected to a subsequent reaction after purification and/or isolation by conventional means such as extraction, recrystallization, etc.

Other operations in the reaction and other after-treatments can be carried out in the same manners as those so far usually used in the same kind of reaction as the above reaction.

The polymer of the present invention comprising monomer units of the above formula [1a] according to the present invention as constituent units, includes homopolymers comprising monomer units of the formula [1a] as constituent units, copolymers comprising two or more kinds of monomer units of the formula [1a] as constituent units, copolymers comprising as constituent units one or more kinds of monomer units of the formula [1a] and one or more kinds of monomer units of the formula [1b]:

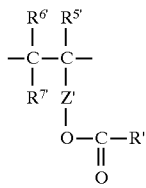

wherein $R^5$, $R^6$, $R^7$ and Z have the same meanings as those of $R^5$, $R^6$, $R^7$ and Z, respectively, defined in the formula [1a]; and R' is a hydroxyalkyl group, and copolymers comprising as constituent units one or more kinds of monomer units of the formula [1a] and one or more kinds of monomer units of the formula [6a]:

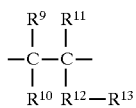

wherein $R^9$ is a hydrogen atom, a lower alkyl group or a halogen atom; $R^{10}$ is a hydrogen atom, a lower alkyl group, a halogen atom, a carboxyl group, an alkyloxycarbonyl group or a formyl group; $R^{11}$ is a hydrogen atom, a lower alkyl group, a carboxyl group, an alkyloxycarbonyl group or a halogen atom; $R^{12}$ is an alkylene group which may have a double bond, or a direct link; and $R^{13}$ is a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, an aryloxycarbonyl group, an acyloxy group, a cyano group, a carboxyl group, a formyl group, an amino group, a sulfonic acid group, a carbamoyl group or a hydroxyl group, and $R^{10}$ and $R^{13}$ may form together a group of the formula: —CO—O—CO— or —CO—NH—CO—.

The hydroxyalkyl group represented by R' in the formula [1b], includes those represented by the formula [2a]:

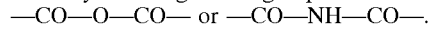

wherein $R^{1'}$ and $R^{2'}$ have the same meaning as those of $R^1$ and $R^2$, respectively, defined above.

Specific examples of $R^{1'}$, $R^{2'}$, $R^{5'}$, $R^{6'}$, $R^{7'}$ and Z' are the same as the above specific examples of $R^1$, $R^2$, $R^5$, $R^6$, $R^7$ and Z, respectively.

In the formula [6a], the lower alkyl group represented by each of $R^9$, $R^{10}$ and $R^{11}$ may be linear or branched and includes, for example, alkyl groups having 1 to 6 carbon atoms. Specific examples thereof are a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, a n-hexyl group, an isohexyl group, etc.

The halogen atom represented by each of $R^9$, $R^{10}$, $R^{11}$ and $R^{13}$ includes fluorine, chlorine, bromine, iodine, etc.

The alkyloxycarbonyl group represented by each of $R^{10}$, $R^{11}$ and $R^{13}$ may be linear, branched or cyclic and may have 1 to 3 double bonds. Examples thereof are alkyloxycarbonyl groups having 2 to 19 carbon atoms. The cyclic alkyloxycarbonyl group may be monocyclic or polycyclic and includes, for example, alicyclic alkyloxycarbonyl groups having 6 to 14 carbon atoms. Specific examples of the alkyloxycarbonyl group are a methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, an ethenyloxycarbonyl group, a propenyloxycarbonyl group, a butenyloxycarbonyl group, a tert-butyloxycarbonyl group, a 2-ethylhexyloxycarbonyl group, a cyclohexyloxycarbonyl group, a tricyclodecanyloxycarbonyl group, an adamantyloxycarbonyl group, a norbornyloxycarbonyl group, a bicyclo[3.2.1] octenyloxycarbonyl group, a bicyclo[2.2.2] octyloxycarbonyl group, a menthyloxycarbonyl group, an isobornyloxycarbonyl group, etc.

The alkyl group represented by $R^{13}$ may be linear, ranched or cyclic and may have a double bond. Examples thereof are alkyl groups having 1 to 20 carbon atoms. Specific examples thereof are a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, a heptyl group, an octyl group, a nonyl group, a decyl group, an undecyl group, a dodecyl group, a hexadecyl group, an octadecyl group, a cyclopropyl group, a cyclopentyl group, a cyclohexyl group, an ethenyl group, a propenyl group, a butenyl group, a pentenyl group, a hexenyl group, a heptenyl group, an octenyl group, etc.

The haloalkyl group represented by $R^{13}$ includes, for example, haloalkyl groups of 1 to 20 carbon atoms formed by halogenation (for example, fluorination, chlorination, bromination or iodination) of the above-exemplified alkyl groups. Specific examples thereof are a chloromethyl group, a bromomethyl group, a trifluoromethyl group, a 2-chloroethyl group, a 3-chloropropyl group, a 3-bromopropyl group, a 3,3,3-trifluoropropyl group, a 2-perfluorooctylethyl group, a perfluorooctyl group, a 1-chlorodecyl group, a 1-chlorooctadecyl group, etc.

The aryl group represented by $R^{13}$ includes, for example, a phenyl group, a tolyl group, a xylyl group, a naphthyl group, an anthryl group, a 4-ethylphenyl group, a 4-methoxyphenyl group, a 4-vinylphenyl group, a 4-chlorophenyl group, etc.

The aliphatic heterocyclic group represented by $R^{13}$ is preferably, for example, a 5-membered or 6-membered aliphatic heterocyclic group. Examples thereof are aliphatic heterocyclic groups containing 1 to 3 heteroatoms such as nitrogen, oxygen, sulfur, etc. Specific examples thereof are a pyrrolidyl-2-one group, a piperidino group, a morpholino group, etc.

The aromatic heterocyclic group represented by $R^{13}$ is preferably, for example, a 5-membered or 6-membered aromatic heterocyclic group. Examples thereof are aromatic heterocyclic groups containing 1 to 3 heteroatoms such as nitrogen, oxygen, sulfur, etc. Specific examples thereof are a pyridyl group, an imidazolyl group, a thiazolyl group, a furanyl group, a pyranyl group, etc.

The aralkyloxycarbonyl group represented by $R^{13}$ includes, for example, aralkyloxycarbonyl groups having 8 to 20 carbon atoms. Specific examples thereof are a benzyloxycarbonyl group, a phenethyloxycarbonyl group, etc.

The acyloxy group represented by $R^{13}$ is preferably, for example, an acyloxy group of 2 to 18 carbon atoms derived from a carboxylic acid. Specific examples thereof are an acetyloxy group, a propionyloxy group, a butyryloxy group, a pentanoyloxy group, a hexanoyloxy group, a heptanoyloxy group, an octanoyloxy group, a lauroyloxy group, a stearoyloxy group, a benzoyloxy group, etc.

The hydroxyalkyloxycarbonyl group represented by $R^{13}$ includes hydroxyalkyloxycarbonyl groups of 2 to 18 arbon atoms formed by replacement of the hydrogen atom of the above-exemplified alkyloxycarbonyl group by a hydroxyl group. Specific examples thereof are a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxydodecyloxycarbonyl group, a hydroxyoctadecyloxycarbonyl group, etc.

The aryloxycarbonyl group represented by $R^{13}$ is preferably, for example, an aryloxycarbonyl group having 7 to 15 carbon atoms. Specific examples thereof are a phenyloxycarbonyl group, a naphthyloxycarbonyl group, etc.

The alkylene group which may have a double bond and is represented by $R^2$ may be linear or branched and includes, for example, alkylene groups of 1 to 10 carbon atoms. The alkylene group having a double bond includes those having one or more double bonds, preferably 1 to 5 double bonds, more preferably 1 to 3 double bonds, at arbitrary positions in the chain. Specific examples thereof are a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, an ethenylene group, a propenylene group, a butenylene group, a pentenylene group, a hexenylene group, a butadienylene group, etc.

The monomer unit of the formula [6a] is derived from a monomer of the formula [6]:

wherein $R^9$ through $R^{13}$ are as defined above. Specific examples of this monomer are ethylenically unsaturated aromatic hydrocarbons having 8 to 20 carbon atoms, such as styrene, 4-methylstyrene, 4-ethylstyrene, 4-methoxystyrene, and divinylbenezene; alkenyl esters having 3 to 20 carbon atoms, such as vinyl formate, vinyl acetate, vinyl propionate, and isopropenyl acetate; halogen-containing ethylenically unsaturated compounds having 2 to 20 carbon atoms, such as vinyl chloride, vinylidene chloride, vinylidene fluoride, tetrafluoroethylene, and tetrachloroethylene; ethylenically unsaturated carboxylic acids having 3 to 20 carbon atoms, such as acrylic acid, methacrylic acid, itaconic acid, maleic acid, fumaric acid, crotonic acid, citraconic acid, mesaconic acid, vinylacetic acid, allylacetic acid, and vinylbenzoic acid [each of these acids may be in the form a salt such as an alkali metal salt (e.g. sodium salt or potassium salt), an ammonium salt or the like]; ethylenically unsaturated carboxylic acid esters having 4 to 20 carbon atoms, such as methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, phenyl methacrylate, benzyl methacrylate, adamantyl methacrylate, tricyclodecanyl methacrylate, menthyl methacrylate, norbornyl methacrylate, isobornyl methacrylate, methyl acrylate, ethyl acrylate, butyl acrylate, 2-ethylhexyl acrylate, lauryl acrylate, stearyl acrylate, vinyl acrylate, adamantyl acrylate, tricyclodecanyl acrylate, menthyl acrylate, norbornyl acrylate, isobornyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl mesaconate, diethyl mesaconate, methyl 3-butenoate, 2-hydroxyethyl methacrylate, 3-hydroxypropyl methacrylate, 2-hydroxypropyl methacrylate, 2-hydroxyethyl acrylate, 3-hydroxypropyl acrylate, and 2-hydroxypropyl acrylate; cyano-containing ethylenically unsaturated compounds having 3 to 20 carbon atoms, such as acrylonitrile, methacrylonitrile, and allyl cyanide; ethylenically unsaturated amide compounds having 3 to 20 carbon atoms, such as acrylamide, methacrylamide, and maleimide; ethylenically unsaturated aldehydes having 3 to 20 carbon atoms, such as acrolein, and crotonaldehyde; ethylenically unsaturated sulfonic acids having 2 to 20 carbon atoms, such as vinylsulfonic acid, and 4-vinylbenzenesulfonic acid (each of these acids may be in the form of a salt, for example, an alkali metal salt such as sodium salt, potassium salt); ethylenically unsaturated aliphatic amines having 2 to 20 carbon atoms, such as vinylamine, and allylamine; ethylenically unsaturated aromatic amines having 8 to 20 carbon atoms, such as vinylaniline; ethylenically unsaturated aliphatic heterocyclic amines having 5 to 20 carbon atoms, such as N-vinylpyrrolidone, and vinylpiperidine; ethylenically unsaturated aromatic heterocyclic amines having 5 to 20 carbon atoms, such as vinylpyridine, and 1-vinylimidazole; ethylenically unsaturated alcohols having 3 to 20 carbon atoms, such as allyl alcohol, and crotyl alcohol; ethylenically unsaturated phenols having 8 to 20 carbon atoms, such as 4-vinylphenol; and diene type compounds having 4 to 20 carbon atoms, such as butadiene, and isoprene.

When the polymer of the present invention is used as a resist material, especially preferable examples thereof are copolymers comprising as constituent units monomer units of the formula [1a] and comonomer units of the formula [1b] wherein $R^{5'}$, $R^{6'}$, $R^{7'}$ and $Z'$ have the same meanings as of $R^5$, $R^6$, $R^7$ and Z respectively, defined in the formula [1a]; and copolymers comprising as constituent units monomer units of the formula [1a], comonomer units of the formula [1b] wherein $R^{5'}$, $R^{6'}$, $R^{7'}$ and Z have the same meanings as those of $R^5$, $R^6$, $R^7$ and Z, respectively, defined in the formula [1a], and one or two kinds of comonomer units of the formula [6a].

When the polymer of the present invention is used as a resist material for ArF excimer laser beams, the monomer(s) other than the monomer of the present invention which is polymerized in combination with the monomer of the present invention is preferably a monomer(s) containing no aromatic group.

Specific examples of the polymer of the present invention are polymers having, for example, any of the following combinations of segments.

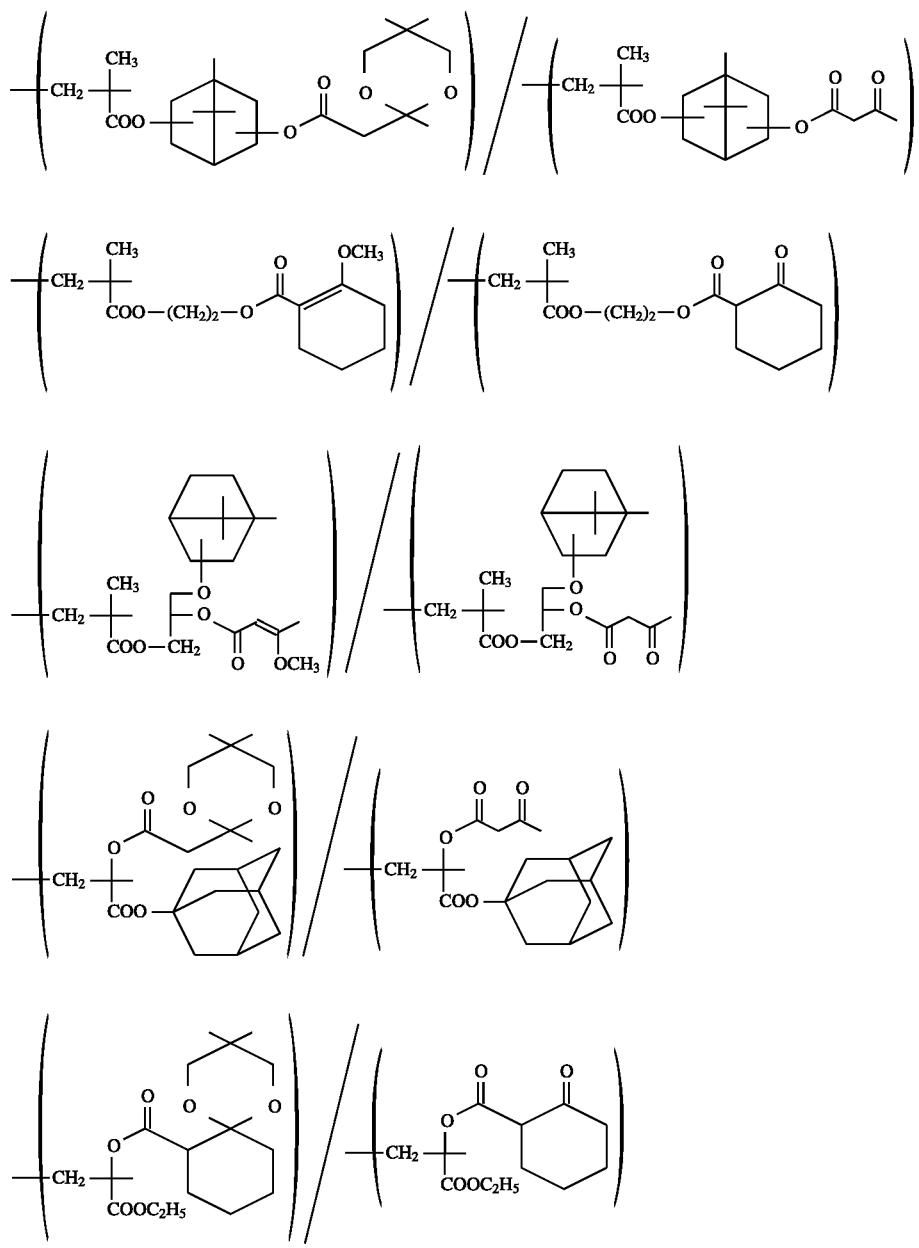

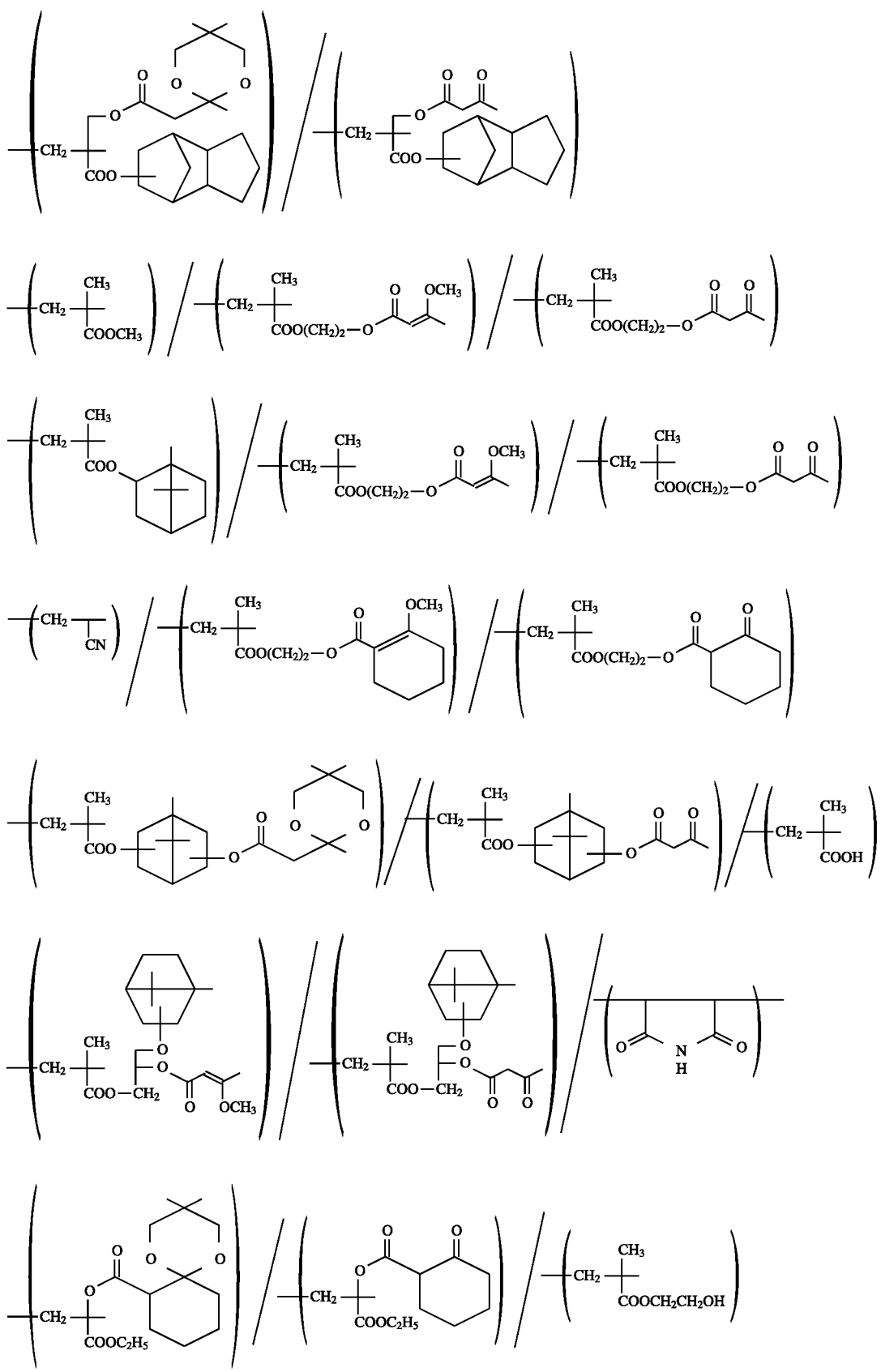

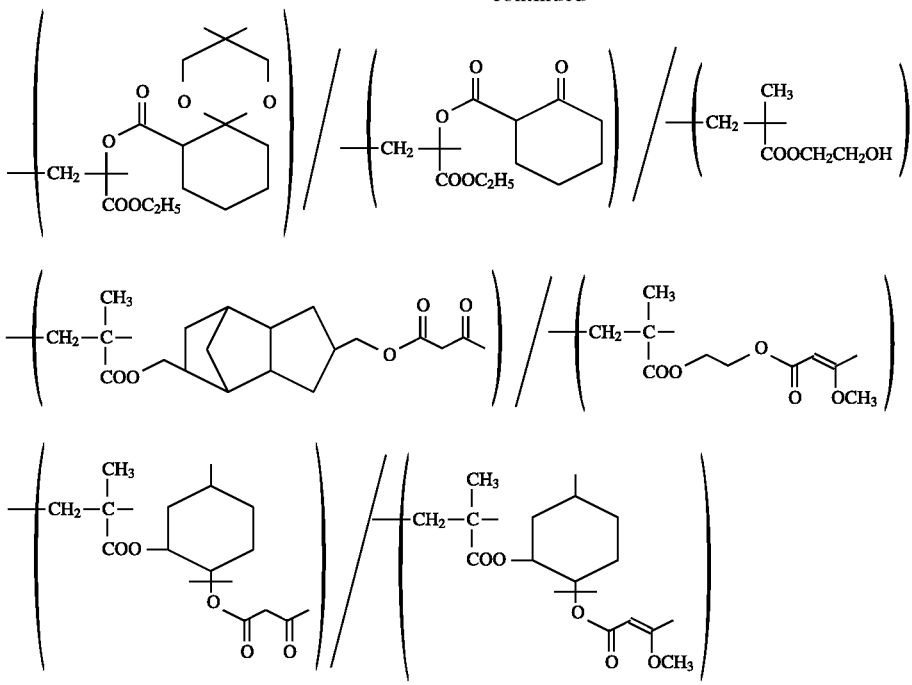

The polymer of the present invention can be obtained by, for example, either of the processes described in the following items (a) and (b).

(a) Process-1

The monomer(s) of the present invention and optionally one or more comonomers are polymerized by a conventional method at 20° C. to 150° C. for 0.5 to 20 hours in a suitable solvent in the presence of a catalytic amount of a free-radical initiator optionally in an inert gas atmosphere. After completion of the reaction, an after-treatment is carried out according to a conventional polymer-collecting method, whereby a desired polymer comprising monomer units of the formula [1a] as constituent units can be obtained.

The free-radical initiator includes, for example, azo polymerization initiators such as azobisisobutyronitrile, 2,2'-azobis(2,4-dimethylvaleronitrile), 2,2'-azobis(methyl 2-methylpropionate), 2,2'-azobis(2-methylbutyronitrile), and 2,2'-azobis(2,4-dimethyl-4-methoxyvaleronitrile); and peroxide type polymerization initiators such as lauroyl peroxide, benzoyl peroxide, bis(4-tert-butylcyclohexyl) peroxydicarbonate, and tert-butyl peroxy-2-ethylhexanoate.

As the solvent for reaction, there can be exemplified organic solvents, for example, hydrocarbons such as benzene, toluene, and xylene; esters such as ethyl acetate, and n-butyl acetate; ethers such as ethyl ether, 1,2-dimethoxyethane, tetrahydrofuran, 1,4-dioxane, and 1,3-dioxolane; alcohols such as ethanol, n-propanol, isopropanol, n-butanol, sec-butanol, isobutanol, and tert-butanol; and ketones such as methyl ethyl ketone, and methyl isobutyl ketone.

When the polymerization is carried out in an inert gas atmosphere, the inert gas includes, for example, nitrogen gas, an argon gas, etc.

(b) Process-2

The monomer(s) of the present invention and optionally one or more comonomers are polymerized by a conventional method at −78° C. to 0° C. for 0.5 to 20 hours in a suitable organic solvent in the presence of a catalytic amount of an organometallic catalyst optionally in an inert gas atmosphere. After completion of the reaction, an after-treatment is carried out according to a conventional polymer-collecting method, whereby a desired polymer comprising monomer units of the formula [1a] as constituent units can be obtained.

The organometallic catalyst includes, for example, organometallic compounds of alkali metals, such as n-butyllithium, sec-butyllithium, tert-butyllithium, sodium naphthalenide, potassium naphthalenide, and cumylpotassium.

The organic solvent includes, for example, ethers such as ethyl ether, 1,2-dimethoxyethane, tetrahydrofuran, 1,4-dioxane, and 1,3-dioxolane; ketones such as methyl ethyl ketone, methyl isobutyl ketone, and acetone; esters such as ethyl acetate, and n-butyl acetate; and hydrocarbons such as benzene, toluene, and xylene. These solvents are preferably used in a dried state.

When the polymerization is carried out in an inert gas atmosphere, the inert gas includes, for example, a nitrogen gas, an argon gas, etc.

Although the concentrations at polymerization of the monomer(s) of the present invention and the comonomer(s) are not particularly limited in either Process-1 or Process-2, they are properly chosen so that the total concentration of the monomer(s) of the present invention and the comonomer(s) may ranges usually from 5 to 95% by weight, preferably from 10 to 90% by weight, based on the weight of the solvent.

Although the molecular weight of the present invention's polymer comprising monomer units of the formula [1a] as constituent units is not particularly limited, its weight-average molecular weight is usually 1,000 to 300,000, preferably 3,000 to 50,000, more preferably 5,000 to 30,000. Although not particularly limited, the degree of polymerization is usually 3 to 1,500, preferably 6 to 250.

In the polymer of the present invention obtained by polymerizing the monomer(s) of the present invention and the comonomer(s), the proportion of monomer units of the formula [1a] of the present invention and the proportion of comonomer units are not particularly limited. When the obtained polymer is used as a resist material, the proportions are as follows. When the polymer is a copolymer comprising one kind each of monomer units of the formulae [1a] and [1b], the proportion of the monomer units of the formula [1a] is 10 to 95 mol %, preferably 20 to 80 mol %, based on the total amount of the monomer units of the formulae [1a] and [1b]. When the polymer is a copolymer comprising one or more kinds each of monomer units of the formulae [1a], [1b] and [6a], the proportion of the sum of the monomer units of the formulae [1a] and [6a] is 10 to 95 mol %, preferably 20 to 70 mol %, based on the total amount of the monomer units of the formulae [1a], [1b] and [6a], and the proportion of the monomer units of the formula [6a] is 1 to 25 mol %, preferably 2 to 20 mol %, based on the total amount of the monomer units of the formulae [1a], [1b] and [6a].

The polymer of the present invention thus obtained is characterized by having in the molecule the protected hydroxyalkyl groups represented by, for example, the formula [2] or [3].

That is, when the polymer of the present invention is used as a resist material, the protecting group of each protected hydroxyalkyl group represented by the formula [2] or [3] in the polymer is removed by an acid generated by exposure to light, so that the protected hydroxyalkyl group becomes a group having substantially the same $pK_a$ value (12 to 13) as that of the phenolic hydroxyl group as soluble group of a conventional novolak or phenolic resin.

Therefore, the presence of the protected hydroxyalkyl group represented by the formula [2] or [3] in the polymer of the present invention permits employment of a 2.38% aqueous TMAH solution, a conventional alkali developing solution, for a developing treatment after exposure to light. Thus, it has become possible to provide a resist material having an easily controllable dissolution rate and excellent dissolving properties during alkali development.

A resist composition comprising the above-mentioned polymer of the present invention, a photosensitive compound which generates an acid upon exposure to light, and a solvent capable of dissolving them is very effectively usable as a resist material for ArF excimer laser beams which is hopeful as an exposure technique for coming generation.

When the polymer of the present invention is used in the resist composition, the photosensitive compound capable of generating an acid upon exposure to light (hereinafter abbreviated as "photoacid generator") which is used in combination with the polymer may be any compound, so long as it has no undesirable influence on the formation of a resist pattern. Preferable examples of the photoacid generator are those which have a sufficient transmittance for light of, in particular, near 193 nm to maintain the high transparency of the resist composition, or is sufficiently increased in transmittance for light of near 193 nm to maintain the high transparency of the resist composition.

As such photoacid generators especially preferable in the present invention, there can be exemplified sulfonium salts such as commercially available trimethylsulfonium-trifluoromethanesulfonate, triphenylsulfonium-trifluoromethanesulfonate, cyclohexylmethyl(2-oxocyclohexyl)sulfonium-trifluoromethanesulfonate, cyclopentylmethyl(2-oxocyclohexyl)sulfonium-trifluoromethanesulfonate, and 2-oxocyclohexylmethyl(2-norbornyl)-sulfonium-trifluoromethanesulfonate; sulfonic acid imide compounds such as trifluoromethylsulfonyloxy-7-oxabicyclo-[2.2.1]hept-5-ene-2,3-dicarboxyimide, trifluoromethylsulfonyloxybicyclo[2.2.1]hept-5-ene-2,3-carboxyimide, and trirluoromethylsulfonyloxysuccinimide; and diazodisulfone compounds such as 1-cyclohexylsulfonyl-1-(1,1-dimethyl-ethylsulfonyl) diazomethane, bis(1,1-dimethylethylsulfonyl)-diazomethane, bis(1-methylethylsulfonyl)diazomethane, bis cyclohexylsulfonyl)diazomethane, bis(isopropyl-sulfonyl) diazomethane, bis(tert-butylsulfonyl)diazomethane, tert-butylsulfonylmethylsulfonyldiazomethane, and cyclohexyl-sulfonylethylsulfonyldiazomethane.

As the solvent used when the polymer of the present invention is used in the resist composition, any solvent may be used so long as it can dissolve both the polymer of the present invention and the photoacid generator. Usually, there are preferably used solvents which have good film-forming properties and cannot absorb light at about 190 nm to about 400 nm. Specific examples of the solvent are methyl Cellosolve acetate, ethyl Cellosolve acetate, propylene glycol monomethyl ether acetate, propylene glycol monoethyl ether acetate, methyl lactate, ethyl lactate, 2-ethoxyethyl acetate, methyl pyruvate, ethyl pyruvate, methyl 3-methoxypropionate, ethyl 3-methoxypropionate, N,N-dimethylformamide, N,N-dimethyl-acetamide, N-methyl-2-pyrrolidone, cyclohexanone, methyl ethyl ketone, 2-heptanone, 1,4-dioxane, diethylene glycol monomethyl ether, diethylene glycol dimethyl ether, ethylene glycol monoisopropyl ether, etc.

Although the resist composition comprising the polymer of the present invention usually comprises as main constituents the above-mentioned three components, i.e., the polymer of the present invention, the photoacid generator and the solvent, it may, if necessary, contain ultraviolet absorbers.

Specific examples of the ultraviolet absorbers are 9-diazofluorene, its derivatives, 1-diazo-2-tetralone, 2-diazo-1-tetralone, 9-diazo-10-phenanthrone, benzophenone, 9-(2-methoxyethoxy)methylanthracene, 9-(2-ethoxyethoxy)methylanthracene, 9-(4-methoxybutoxy) methylanthracene, 9-anthracenemethyl acetate, etc.

If necessary, the resist composition comprising the polymer of the present invention may further contain one or more kinds of sensitivity adjustors, plasticizers, organic acids and surfactants, which are usually used in the art.

The sensitivity adjustors include, for example, polyvinylpyridine, poly(vinylpyridine/methyl methacrylate), pyridine, piperidine, triethylamine, tri-n-propylamine, tri-n-butylamine, trioctylamine, tribenzylamine, dicyclohexylamine, dicyclohexylmethylamine, tetra-methylammonium hydroxide, tetraethylammonium hydroxide, tetra-n-butylammonium hydroxide, N-methyl-2-pyrrolidone, etc.

The plasticizers include, for example, diethyl phthalate, dibutyl phthalate, dipropyl phthalate, etc.

The organic acids include, for example, salicylic acid, lactic acid, 2-hydroxynaphthalene-3-carboxylic acid, 2-nitrobenzoic acid, phthalic acid, succinic acid, malonic acid, etc.

The surfactants include, for example, various commercially available nonionic surfactants, cationic surfactants, anionic surfactants and various fluorine-containing surfactants which are on the market by trade names of, for example, Fluorad (a trade name, mfd. by SUMITOMO 3M Co., Ltd.), EFTOP (a trade name, mfd. by TOHKEM PRODUCTS Corporation), SURFLON (a trade name, mfd. by Asahi Glass Co., Ltd.), Ftergent (a trade name, mfd. by Neos Co., Ltd.), MEGAFAC (a trade name, mfd. by Dainippon Ink and Chemicals, Inc.), UNIDYNE (a trade name, mfd. by DAIKIN INDUSTRIES, LTD.), etc.

By use of the resist composition using the polymer of the present invention, a pattern is formed, for example, as follows.

The resist composition comprising the polymer of the present invention is coated on a semiconductor substrate such as silicon wafer to a thickness of approximately 0.3 to 2.0 $\mu$m (approximately 0.1 to 0.5 $\mu$m when used as a top layer among three layers), and pre-baked in an oven at 70° C. to 130° C. for 10 to 30 minutes, or on a hot plate at 60° C. to 150° C., preferably 60° C. to 110° C., for 60 to 180 seconds.

Then, a mask for forming a desired pattern is put over the resist film thus formed, and the resist film is exposed to, for example, deep ultraviolet light having a wavelength of 220 nm or less, at an exposure dose of approximately 1 to 100 mJ/cm$^2$, followed by baking on a hot plate at 60° C. to 150° C., preferably 60° C. to 110° C., for 60 to 180 seconds.

Subsequently, using a developing solution such as a 0.1 to 5% aqueous tetramethylammonium hydroxide (TMAH) solution, the resist film is developed for about 0.5 to about 3 minutes by a conventional method such as a dip method, a puddle method or a spray method to form the desired pattern on the substrate.

The blending proportions of the polymer of the present invention and the photoacid generator in the resist composition are properly chosen so that the proportion of the photoacid generator may be 1 to 30 parts by weight, preferably 1 to 20 parts by weight, per 100 part by weight of the polymer.

The amount of the solvent in the resist composition according to the present invention is not particularly limited so long as it does not cause a trouble when a positive type resist material obtained by dissolving the polymer of the present invention and the photoacid generator in the solvent is coated on a substrate. The amount is usually 1 to 20 parts by weight, preferably 1.5 to 10 parts by weight, per part by weight of the polymer.

As the developing solution used in the pattern formation process employing any of the above-mentioned arious development methods, an aqueous alkali solution having a suitable concentration which can create a large difference in solubility between light exposed areas and non-exposed areas, is chosen depending on the solubility of the resist material in alkali developing solutions. The concentration is usually 0.01 to 20% by weight. As the aqueous alkali solution used, there can be exemplified aqueous solutions containing, for example, organic amines such as tetramethylammonium hydroxide (TMAH), tetraethyl-ammonium hydroxide, tetrapropylammonium hydroxide, tetrabutylammonium hydroxide, choline, triethanolamine, morpholine, and 1-methylmorpholine; or inorganic alkali compounds such as sodium hydroxide, and potassium hydroxide.

The semiconductor substrate includes, for example, silicon wafers, polycrystalline silicon substrates, TiN substrates, BPSG substrates, etc. These semiconductor substrates are preferably previously treated with a substrate-treating agent such as hexamethyldisilazane (HMDS).

As described above, the protecting group of the protected hydroxyalkyl group represented by the formula [2] or [3] in the polymer of the present invention is removed by an acid generated by exposure to light, so that the protected hydroxyl group becomes a β-ketoester group. Owing to the tautomerism of the β-ketoester group, there is formed an enolic hydroxyl group having substantially the same pK$_a$ value (12 to 13) as that of the phenolic hydroxyl group as soluble group of a conventional novolak or phenolic resin. Therefore, the resist composition comprising the polymer of the present invention permits employment of a 2.38% aqueous TMAH solution, a conventional alkali developing solution, for a developing treatment after exposure to light, namely, its dissolution rate in alkali development is controllable. That is, since a satisfactory resist pattern can be obtained by use of the resist composition comprising the polymer of the present invention, it becomes possible to produce a semiconductor device such as a semiconductor integrated circuit having a higher degree of integration.

It was confirmed that in the resist composition comprising the polymer of the present invention, an acid is generated not only by exposure to deep ultraviolet light or KrF excimer laser beams but also by exposure to electron beams or soft X-rays, and causes chemical amplification. Therefore, the resist composition according to the present invention is a resist material which makes it possible to form a pattern by exposure to deep ultraviolet light, KrF excimer laser beams, electron beams or soft X-rays at a low exposure dose by utilizing the chemical amplification.

The resist material comprising the polymer of the present invention is explained below by giving specific examples. In an area exposed to deep ultraviolet light having a wavelength of 220 nm or less, such as ArF excimer laser beams ($\lambda$=193 nm), an acid is generated, for example, by a photoreaction represented by [Equation 1], [Equation 2] or [Equation 3]:

[Equation 1]

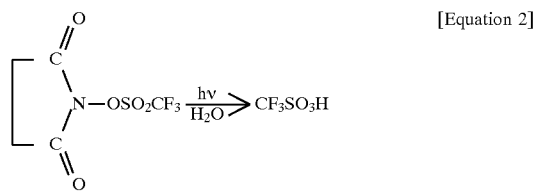

[Equation 2]

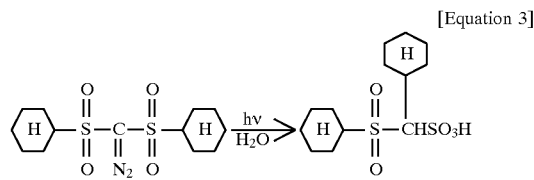

[Equation 3]

When heat treatment is carried out after the exposure, the specified functional group of the polymer of the present invention undergoes deblocking by the acid through reactions represented by the following [Equation 4] and [Equation 5], and the polymer thus made alkali-soluble is dissolved in a developing solution during development.

[Equation 4]

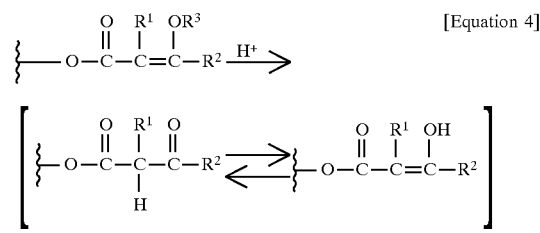

[Equation 4]

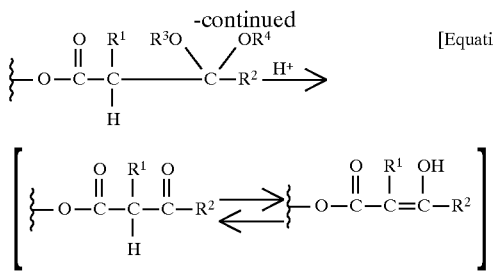
[Equation 5]

On the other hand, in the non-exposed area, no acid is generated, so that the heat treatment does not cause the chemical change. Thus, when a pattern is formed using the resist composition comprising the polymer of the present invention, there is a difference between the exposed area and the non-exposed area in solubility in the alkali developing solution. Consequently, a positive pattern having a satisfactory contrast is formed.

The present invention is explained below in further detail with reference to Examples and Application Examples, which are not by way of limitation but by way of illustration.

The photoacid generator used in Application Examples was synthesized by the process described, for example, in JP-A 7-25846, T. M. Chapman et al., Synthesis, 1971, p.591, and T. M. Chapman et al., J. Org. Chem., 38, 3908 (1973).

EXAMPLE 1

Synthesis of 2-(methacryloyloxy)ethyl 3-methoxy-2-butenoate

With 32.1 g (150 mmol) of 2-(methacryloyloxy)ethyl acetoacetate was mixed 49 ml (450 mmol) of methyl orthoformate, followed by adding thereto 1.74 g (7.5 mmol) of camphorsulfonic acid, and the reaction was carried out with stirring at room temperature for 5 hours. After completion of the reaction, the reaction mixture was diluted with 100 ml of toluene, washed successively with two 50-ml portions of a saturated aqueous sodium hydrogen-carbonate solution, 50 ml of water and 50 ml of a saturated aqueous sodium chloride solution, and dried over anhydrous magnesium sulfate. The solvent was distilled off under reduced pressure and the resulting crude product was purified by a column chromatography [packing: Wakogel C-200 (a trade name, Wako Pure Chemical Industries Ltd.); eluent: n-hexane/ethyl acetate =4/1] to obtain 13.7 g (yield: 40.0%) of the desired compound 2-(methacryloyloxy)ethyl 3-methoxy-2-butenoate as a pale yellow oil.

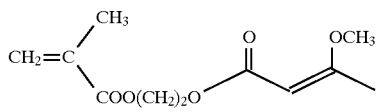

$^1$H-NMR δppm (CDCl$_3$, 270 MHz):
1.96 (s, 3H), 2.29 (s, 3H), 3.64 (s, 3H), 4.33–4.39 (m, 4H), 5.04 (s, 1H), 5.59 (s, 1H), 6.14 (s, 1H).

EXAMPLE 2

Synthesis of 2-(methacryloyloxy)ethyl 3,3-ethylenedioxybutenoate

In 100 ml of toluene were dissolved 21.4 g (100 mmol) of 2-(methacryloyloxy)ethyl acetoacetate and 18.62 g (300 mmol) of ethylene glycol, followed by pouring thereinto 0.19 g (1 mmol) of p-toluenesulfonic acid monohydrate, and the reaction was carried out with refluxing for 2 hours while removing the by-produced water by use of a Dean-Stark trap. After completion of the reaction, the reaction mixture was washed successively with 50 ml of a saturated aqueous sodium hydrogencarbonate solution, two 50-ml portions of water and 50 ml of a saturated aqueous sodium chloride solution, and dried over anhydrous magnesium sulfate. The solvent was distilled off and the resulting crude product was purified by a column chromatography [packing: Wakogel C-200 (a trade name, Wako Pure Chemical Industries Ltd.); eluent: n-hexane/ethyl acetate=3/2] to obtain 19.44 g (yield: 75.3%) of the desired compound 2-(methacryloyloxy)ethyl 3,3-ethylenedioxybutanoate as a pale yellow oil.

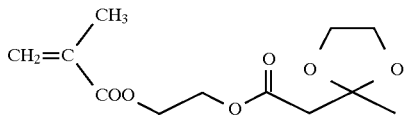

$^1$H-NMR δppm (CDCl$_3$, 270 MHz):
1.51 (s, 3H), 1.95 (s, 3H), 2.71 (s, 2H), 3.98 (s, 4H), 4.36 (s, 4H), 5.59 (S, 1H), 6.14 (s, 1H).

EXAMPLE 3

Synthesis of 2-(methacryloyloxy)ethyl 3,3-(2',2'-dimethylpropylenedioxy)butanoate In 100 ml of toluene were dissolved 21.4 g (100 mmol) of 2-(methacryloyloxy)ethyl acetoacetate and 31.25 g (300 mmol) of 2,2-dimethylpropylene glycol, followed by pouring thereinto 0.19 g (1 mmol) of p-toluenesulfonic acid monohydrate and 0.5 g of phenothiazine, and the reaction was carried out with refluxing for 2 hours while removing the by-produced water by use of a Dean-Stark trap. After completion of the reaction, the reaction mixture was washed successively with 50 ml of a saturated aqueous sodium hydrogencarbonate solution, two 50-ml portions of water and 50 ml of a saturated aqueous sodium chloride solution, and dried over anhydrous magnesium sulfate. The solvent was distilled off and the resulting crude product was distilled under reduced pressure to obtain 20.69 g (yield: 68.9%) of the desired compound 2-(methacryloyloxy)ethyl 3,3-(2',2'-dimethylpropylenedioxy)butanoate as a pale yellow oil.

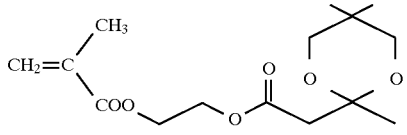

Boiling point: 151°–156° C./4 mmHg.
$^1$H-NMR δppm (CDCl$_3$, 270 MHz):
0.94, 0.98 (s, 3H×2), 1.54 (s, 3H), 1.95 (s, 3H), 2.82 (s, 2H), 3.98 (s, 4H), 4.36 (s, 4H), 5.59 (s, 1H), 6.13 (s, 1H).

EXAMPLE 4

Synthesis of 4-(3-methoxy-2-butenoyloxymethyl)-8-(methacryloyloxymethyl)tricyclo[5.2.1.0$^{2,6}$]decane (1) In 600 ml of anhydrous tetrahydrofuran were dissolved 98.15 g (0.50 mol) of tricyclo[5.2.1.0$^{2,6}$]decane-4,8-dimethanol and 41.53 g (525 mmol) of pyridine, and the resulting solution was cooled to 5° C. or lower, followed by adding dropwise thereto 52.27 g (0.50 mol) of methacryloyl chloride over a period of 1 hour. The mixture thus obtained was stirred at the same temperature for another 1 hour and then at room temperature for 6 hours. The pyridinium salt thus formed was filtered off and the mother liquor was concentrated under reduced pressure. The residue was dissolved in 1 liter of methylene chloride, and the resulting solution was washed with 500 ml of 2% hydrochloric acid and then 500 ml of a saturated aqueous sodium chloride solution, and dried over anhydrous magnesium sulfate. The solvent was distilled off and the resulting crude product was purified by a column chromatography [packing: Wakogel C-200 (a trade name, Wako Pure Chemical Industries Ltd.); eluent: n-hexane/ethyl acetate=3/2] to obtain 52.73 g (yield: 39.9%) of desired 8-(methacryloyloxymethyl)tricyclo[5.2.1.0$^{2.6}$]decane-4-methanol as a pale yellow oil.

$^1$H-NMR δppm (CDCl$_3$, 270MHz):
0.83–1.04 (m, 1H), 1.20–1.88 (m, 7H), 1.95 (s, 3H), 2.01–2.22 (m, 4H), 2.32–2.58 (m, 2H), 3.36–3.52 (m, 2H), 3.89–4.02 (m, 2H), 5.55 (s, 1H), 6.10 (s, IH).

(2) In 100 ml of toluene were dissolved 50.23 g (0.19 mol) of the 8-(methacryloyloxymethyl)tricyclo-[5.2.1.0$^{2.6}$]decane-4-methanol obtained in the item (1) and 0.05 g of triethylamine, followed by adding dropwise thereto 16.3 g (193.8 mmol) of diketene at 30° C. over a period of 1 hour, and the reaction was carried out with stirring at the same temperature for 4 hours. After standing overnight, the reaction mixture was washed successively with 100 ml of 1N-H$_2$SO$_4$, four 100-ml portions of water and 100 ml of a saturated aqueous sodium chloride solution, and dried over anhydrous magnesium sulfate. The solvent was distilled off to obtain 66.0 g (yield: 100%) of desired 4-acetoacetoxymethyl-8-(methacryloyloxymethyl)tricyclo[5.2.1.0$^{2.6}$]decane as a pale yellow oil.

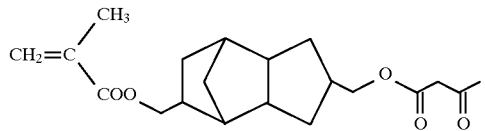

$^1$H-NMR δppm (CDCl$_3$, 270 MHz):
0.87–1.05 (m, 1H), 1.21–1.88 (m, 7H), 1.94 (s, 3H), 1.99–2.24 (m, 4H), 2.27 (s, 3H), 2.30–2.56 (m, 2H), 3.45 (s, 2H), 3.86–4.05 (m, 4H), 5.55 (s, 1H), 6.10 (s, 1H).

(3) In 33 ml (300 mmol) of methyl orthoformate was dissolved 34.84 g (100 mmol) of the 4-acetoacetoxymethyl-8-(methacryloyloxymethyl)tricyclo[5.2.1.0$^{2.6}$]decane obtained in the item (2), followed by pouring thereinto 1.16 g (5 mmol) of camphorsulfonic acid, and the reaction was carried out with stirring at room temperature for 8 hours. After standing overnight, the reaction mixture was diluted with 120 ml of toluene, washed successively with two 50-ml portions of a saturated aqueous sodium hydrogen-carbonate solution, 50 ml of water and 50 ml of a saturated aqueous sodium chloride solution, and dried over anhydrous magnesium sulfate. The solvent was distilled off and the resulting crude product was purified by a column chromatography [packing: Wakogel C-200 (a trade name, Wako Pure Chemical Industries Ltd.); eluent: n-hexane/ethyl acetate=4/1] to obtain 10.79 g (yield: 29.8%) of the title compound 4-(3-methoxy-2-butenoyloxymethyl)-8-(methacryloyloxymethyl)tricyclo[5.2.1.0$^{2.6}$]decane as a pale yellow oil.

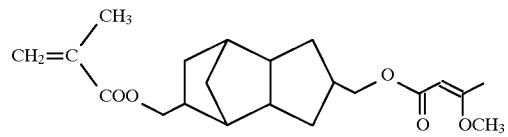

$^1$H-NMR δppm (CDCl$_3$, 270MHz):
0.92–1.08 (m, 1H), 1.21–1.90 (m, 7H), 1.94 (s, 3H), 2.01–2.24 (m, 4H), 2.29 (s, 3H), 2.30–2.58 (m, 2H), 3.64 (s, 3H), 3.84–4.03 (m, 4H), 5.02 (s, 1H), 5.55 (s, 1H), 6.10 (s, 1H).

EXAMPLE 5

Synthesis of 3-(methacryloyloxy)menthan-8-yl 3-methoxy-2-butenoate (1) In 350 ml of anhydrous tetrahydrofuran were dissolved 50.0 g (290 mmol) of menthane-3,8-diol and 24.11 g (305 mmol) of pyridine, and the resulting solution was cooled to 5° C. or lower, followed by adding dropwise thereto 30.34 g (290 mmol) of methacryloyl chloride over a period of 1 hour. The mixture thus obtained was stirred at the same temperature for another 1 hour and then at room temperature for 6 hours. The pyridinium salt thus formed was filtered off and the mother liquor was concentrated under reduced pressure. The residue was dissolved in 600 ml of methylene chloride, and the resulting solution was washed with 300 ml of 2% hydrochloric acid and then 300 ml of a saturated aqueous sodium chloride solution, and dried over anhydrous magnesium sulfate. The solvent was distilled off to obtain 69.0 g (yield: 99%) of desired 3-(methacryloyloxy)menthan-8-ol as a pale yellow oil.

$^1$H-NMR δppm (CDCl$_3$, 270MHz):
0.88 (d, 3H, J=6.59 Hz), 1.15 (s, 3H), 1.20 (s, 3H), 0.92–1.13 (m, 2H), 1.41–1.48 (m, 1H), 1.61–1.88 (m, 4H), 1.96 (s, 3H), 1.94–2.09 (m, 1H), 5.30 (s, 1H), 5.59 (s, 1H), 6.12 (s, 1H).

(2) In 140 ml of toluene were dissolved 67.01 g (280 mmol) of the 3-(methacryloyloxy)menthan-8-ol obtained in the item (1) and 0.57 g of triethylamine, followed by adding dropwise thereto 24.7 g (294 mmol) of diketene at 30° C. over a period of 30 minutes, and the reaction was carried out with stirring at the same temperature for 4 hours. After standing overnight, the reaction mixture was washed successively with 150 ml of 1N-H$_2$SO$_4$, four 150-ml portions of water and 150 ml of a saturated aqueous sodium chloride solution, and dried over anhydrous magnesium sulfate. The solvent was distilled off and the resulting crude product was purified by a column chromatography [packing: Wakogel C-200 (a trade name, Wako Pure Chemical Industries Ltd.); eluent: n-hexane/ethyl acetate=3/2] to obtain 66.5 g (yield: 73.4%) of desired 3-(methacryloyloxy)menthan-8-yl acetoacetate as a pale yellow oil.

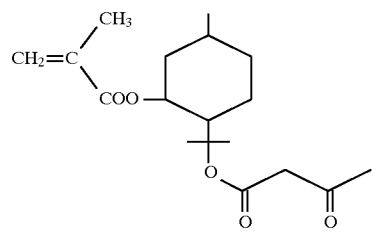

$^1$H-NMR δppm (CDCl$_3$, 270 MHz):
0.87 (d, 3H, J=6.6 Hz), 0.98–1.19 (m, 2H), 1.46 (s, 6H), 1.43–1.51 (m, 1H), 1.60–1.68 (m, 3H), 1.71–1.90 (m, 1H), 1.95 (s, 3H), 2.11–2.17 (m, 1H), 2.24 (s, 3H), 3.37 (s, 2H), 5.36 (s, 1H), 5.58 (s, 1H), 6.11 (s, 1H).

(3) In 66 ml (600 mmol) of methyl orthoformate was dissolved 32.34 g (100 mmol) of the 3-(methacryloyloxy)menthan-8-yl acetoacetate obtained in the item (2), followed by pouring thereinto 1.16 g (5 mmol) of camphorsulfonic acid, and the reaction was carried out with stirring at room temperature for 8 hours. After standing overnight, the reaction mixture was diluted with 120 ml of toluene, washed successively with two 50-ml portions of a saturated aqueous sodium hydrogencarbonate solution, 50 ml of water and 50 ml of a saturated aqueous sodium chloride solution, and dried over anhydrous magnesium sulfate. The solvent was distilled off and the resulting crude product was purified by a column chromatography [packing: Wakogel C-200 (a trade name, Wako Pure Chemical Industries Ltd.); eluent: n-hexane/ethyl acetate=3/2] to obtain 6.75 g (yield: 20.0%) of the title compound 3-(methacryloyloxy)menthan-8-yl 3-methoxy-2-butenoate as a pale yellow oil.

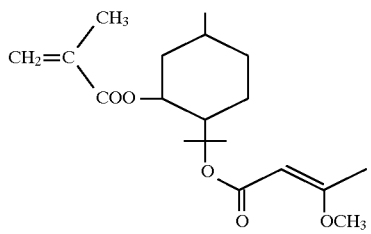

$^1$H-NMR δppm (CDCl$_3$, 270 MHz):
 0.87 (d, 3H, J=6.23 Hz), 1.06–1.19 (m, 2H), 1.45 (s, 6H), 1.43–1.51 (m, 3H), 1.64–1.74 (m, 1H), 1.92–1.99 (m, 1H), 2.17 (s, 3H), 2.18–2.30 (m, 1H), 2.23 (s, 3H), 3.60 (s, 3H), 4.93 (s, 1H), 5.36 (s, 1H), 5.56 (s, 1H), 6.12 (s, 1H).

EXAMPLE 6

Synthesis of a polymer 4.0 Grams (40 mmol) of methyl methacrylate, 11.4 g (50 mmol) of the 2-(methacryloyloxy)ethyl 3-methoxy-2-butenoate obtained in Example 1, 2.14 g (10 mmol) of 2-(methacryloyloxy)ethyl acetoacetate and 60 ml of dry tetrahydrofuran (THF) were mixed and then heated to 65° C., followed by adding thereto 1.97 g (12 mmol) of azobisisobutyronitrile, and the resulting mixture was subjected to polymerization for 5 hours under nitrogen at the same temperature. After completion of the reaction, the reaction mixture was poured into 650 ml of n-hexane to precipitate a polymer. The polymer was collected by filtration and dried to obtain 14.6 g (yield: 83%) of the desired polymer. As a result of $^1$H-NMR measurement, the obtained polymer was found to have methyl methacrylate unit, 2-(methacryloyloxy)ethyl 3-methoxy-2-butenoate unit and 2-(methacryloyloxy)ethyl acetoacetate unit in a molar ratio of approximately 0.47:0.47:0.06. The weight average molecular weight (Mw) of the polymer was 12,700 as determined by a gel permeation chromatography (GPC) method (solvent: tetrahydrofuran) using a polystyrene as a standard. The dispersity was 2.11.

EXAMPLE 7

Synthesis of a polymer 7.67 Grams (22 mmol) of the 4-acetoacetoxymethyl-8-(methacryloyloxymethyl)tricyclo[5.2.1.0$^{2.6}$]decane obtained in Example 4, (2), 4.11 g (18 mmol) of the 2-(methacryloyloxy)ethyl 3-methoxy-2-butenoate obtained in Example 1 and 25 ml of dry tetrahydrofuran (THF) were mixed and then heated to 65° C., followed by adding thereto 0.79 g (4.8 mmol) of azobisisobutyronitrile, and the resulting mixture was subjected to polymerization for 5 hours in a nitrogen atmosphere at the same temperature. After completion of the reaction, the reaction mixture was poured into 300 ml of n-hexane to precipitate a polymer. The polymer was collected by filtration and dried to obtain 9.04 g (yield: 76%) of the desired polymer. As a result of $^1$H-NMR measurement, the obtained polymer was found to have 4-aceto-acetoxymethyl-8-(methacryloyloxymethyl)tricyclo-[5.2.1.0$^{2.6}$]decane unit and 2-(methacryloyloxy)ethyl 3-methoxy-2-butenoate unit in a molar ratio of approximately 0.46:0.54. The weight average molecular weight (Mw) of the polymer was 42,200 as determined by a GPC method (solvent: tetrahydrofuran) using a polystyrene as a standard. The dispersity was 2.96.

EXAMPLE 8

Synthesis of a polymer 9.06 Grams (28 mmol) of the 3-(methacryloyloxy)menthan-8-yl acetoacetate obtained in Example 5, (2), 4.05 g (12 mmol) of the 3-(methacryloyloxy)menthan-8-yl 3-methoxy-2-butenoate obtained in Example 5 and 27 ml of dry tetrahydrofuran (THF) were mixed and then heated to 65° C., followed by adding thereto 0.79 g (4.8 mmol) of azobisisobutyronitrile, and the resulting mixture was subjected to polymerization for 5 hours in a nitrogen gas atmosphere at the same temperature. After completion of the reaction, the reaction mixture was poured into 300 ml of n-hexane to precipitate a polymer. The polymer was collected by filtration and dried to obtain 6.03 g (yield: 46%) of the desired polymer. As a result of $^1$H-NMR measurement, the obtained polymer was found to have 3-(methacryloyloxy)menthan-8-yl acetoacetate unit and 3-(methacryloyloxy)menthan-8-yl 3-methoxy-2-butenoate unit in a molar ratio of approximately 0.62:0.38. The weight average molecular weight (Mw) of the polymer was 12,700 as determined by a GPC method (solvent: tetrahydrofuran) using a polystyrene as a standard. The dispersity was 2.11.

Application Example 1

A resist composition was prepared according to the following recipe:
 (a) the polymer obtained in Example 6 4.0 g
 (b) a photoacid generator 80 mg (triphenylsulfonium trifluoromethanesulfonate)
 (c) ethylene glycol dimethyl ether 15.6 g The resist composition having the above make-up was filtered through a Teflon (a trade name) filter with a pore size of 0.1 μm, and the filtrate was spin-coated on a silicon wafer and then baked on a hot plate at 90° C. for 60 seconds to obtain a resist film of 0.5 μm in thickness.

Subsequently, the wafer having the film formed thereon was allowed to stand in a close-contact type exposure experiment machine sufficiently purged with a nitrogen gas, and the resist film was closely covered with a patterned mask and exposed to ArF excimer laser beams (λ=193 nm; NA 0.55) through the mask at an exposure dose of 16 mJ/cm$^2$. After the exposure, the wafer was heated on a hot plate at 60° C. for 60 seconds, and the film was developed with a developing solution (a 2.38% aqueous TMAH solution having a temperature of 23° C.) for 60 seconds by a puddle method and then rinsed with ultrapure water for 60 seconds to obtain a 0.25 gm (exposure dose: about 14 mJ/cm$^2$) line-and-space pattern.

Application Example 2

A resist composition prepared from the same amounts of the same components (a), (b) and (c) as used in Application Example 1 was filtered through a Teflon (a trade name) filter with a pore size of 0.1 µm, and the filtrate was spin-coated on a silicon wafer and then baked on a hot plate at 90° C. for 60 seconds to obtain a resist film of 0.5 µm in thickness.

Subsequently, the wafer having the film formed thereon was allowed to stand in a close-contact type exposure experiment machine sufficiently purged with a nitrogen gas, and the resist film was closely covered with a patterned mask and exposed to ArF excimer laser beams (λ=193 nm; NA 0.55) through the mask at an exposure dose of 16 mJ/cm$^2$. After the exposure, the wafer was heated on a hot plate at 60° C. for 60 seconds, and the film was developed with a developing solution (a 2.38% aqueous TMAH solution having a temperature of 23° C.) for 60 seconds by a dip method and then rinsed with ultrapure water for 60 seconds to obtain a 0.18 µm (exposure dose: about 17 mJ/cm$^2$) line-and-space pattern.

Application Example 3

A resist composition was prepared according to the following recipe:

(a) the polymer obtained in Example 7 1.0 g (b) a photoacid generator 20 mg (triphenylsulfonium trifluoromethanesulfonate)

(c) ethylene glycol dimethyl ether 4.0 g

The resist composition having the above prepared was filtered through a Teflon (a trade name) filter with a pore size of 0.1 µm, and the filtrate was spin-coated on a silicon wafer and then baked on a hot plate at 90° C. for 60 seconds to obtain a resist film of 0.5 µm in thickness.

Subsequently, the wafer having the film formed thereon was allowed to stand in a close-contact type exposure experiment machine sufficiently purged with a nitrogen gas, and the resist film was closely covered with a patterned mask and exposed to ArF excimer laser beams (λ=193 nm; NA 0.55) through the mask at an exposure dose of 16 mJ/cm$^2$. After the exposure, the wafer was heated on a hot plate at 90° C. for 60 seconds, and the film was developed with a developing solution (a 2.38% aqueous TMAH solution having a temperature of 23° C.) for 60 seconds by a puddle method and then rinsed with ultrapure water for 60 seconds to obtain a 0.25 µm (exposure dose: about 14 mJ/cm$^2$) line-and-space pattern.

Application Example 4

A resist composition was prepared according to the following recipe:

(a) the polymer obtained in Example 8 1.0 g (b) a photoacid generator 20 mg (triphenylsulfonium trifluoromethanesulfonate)

(c) ethylene glycol dimethyl ether 4.0 g

The resist composition having the above prepared was filtered through a Teflon (a trade name) filter with a pore size of 0.1 µm, and the filtrate was spin-coated on a silicon wafer and then baked on a hot plate at 90° C. for 60 seconds to obtain a resist film of 0.5 µm in thickness.

Subsequently, the wafer having the film formed thereon was allowed to stand in a close-contact type exposure experiment machine sufficiently purged with a nitrogen gas, and the resist film was closely covered with a patterned mask and exposed to ArF excimer laser beams (λ=193 nm; NA 0.55) through the mask at an exposure dose of 16 mJ/cm$^2$. After the exposure, the wafer was heated on a hot plate at 110° C. for 60 seconds, and the film was developed with a developing solution (a 2.38% aqueous TMAH solution having a temperature of 23° C.) for 60 seconds by a puddle method and then rinsed with ultrapure water for 60 seconds to obtain a 0.25 µm (exposure dose: about 25 mJ/cm$^2$) line-and-space pattern.

As described above, the present invention provides a novel polymer useful, for example, for preparing a resist composition used for production of semiconductor devices, etc., and a novel monomer usable as a material for said polymer. The resist composition using the polymer of the present invention is very effectively usable as a resist material for ArF excimer laser beams which is hopeful as an exposure technique for coming generation. Therefore, the present invention is of great value, for example, in formation of an ultra-fine pattern in the semiconductor industry, etc.

Furthermore, the polymer of the present invention has chelating ability and hence can be expected to be usable for analytical chemistry, metal separation and purification, etc. as a functional resin for analysis and separation.

What is claimed is:

1. A monomer represented by the formula [1]:

$$\begin{array}{c} R^6 \quad R^5 \\ | \quad | \\ C=C \\ | \quad | \\ R^7 \quad Z \\ | \\ O-C-R \\ \parallel \\ O \end{array} \quad [1]$$

wherein $R^5$, $R^6$ and $R^7$ are independently a hydrogen atom, an alkyl group, a cyano group, an alkyloxycarbonyl group or a carbamoyl group; Z is a spacer or a direct link; and R is a hydroxyalkyl group having a protected terminal hydroxyl group.

2. A monomer according to claim 1, wherein in the formula [1], the hydroxyalkyl group having a protected terminal hydroxyl group which is represented by R is a group represented by the formula [2]:

$$\begin{array}{c} R^1 \quad OR^3 \\ | \quad | \\ -C=C-R^2 \end{array} \quad [2]$$

wherein $R^1$ and $R^2$ are independently a hydrogen atom, a substituted or unsubstituted alkyl group or an alicyclic hydrocarbon group, and $R^1$ and $R^2$ may form together an aliphatic ring; and $R^3$ is an alkyl group, an alkenyl group, a hydroxyalkyl group, an alkyloxycarbonyl group or an alkylsilyl group, or the formula [3]:

$$\begin{array}{c} R^1 \quad R^3O \quad OR^4 \\ | \quad \diagdown \quad \diagup \\ -C \longrightarrow C-R^2 \\ | \\ H \end{array} \quad [3]$$

wherein $R^4$ is an alkyl group; and $R^1$, $R^2$ and $R^3$ are as defined above, and $R^3$ and $R^4$ may form together an aliphatic ring.

3. A monomer according to claim 1, wherein the spacer is a group represented by the formula [4]:

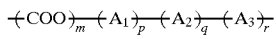    [4]

wherein $A_2$ is a divalent hydrocarbon group which may have one or more oxygen atoms; $A_1$ and $A_3$ are independently a lower alkylene group; m is 0 or 1; and p, q and r are independently 0 or 1, provided that q is 1 in the case of m being 1.

4. A monomer according to claim 1, wherein in the formula [1], the hydroxyalkyl group having a protected terminal hydroxyl group which is represented by R is a group represented by the formula [2]:

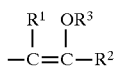    [2]

wherein $R^1$ and $R^2$ are independently a hydrogen atom, a substituted or unsubstituted alkyl group or an alicyclic hydrocarbon group, and $R^1$ and $R^2$ may form together an aliphatic ring; and $R^3$ is an alkyl group, an alkenyl group, a hydroxyalkyl group, an alkyloxycarbonyl group or an alkylsilyl group, or the formula [3]:

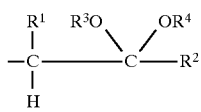    [3]

wherein $R^4$ is an alkyl group; and $R^1$, $R^2$ and $R^3$ are as defined above, and $R^3$ and $R^4$ may form together an aliphatic ring, and the spacer is a group represented by the formula [4]:

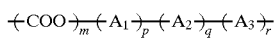    [4]

wherein $A_2$ is a divalent hydrocarbon group which may have one or more oxygen atoms; $A_1$ and $A_3$ are independently a lower alkylene group; m is 0 or 1; and p, q and r are independently 0 or 1, provided that q is 1 in the case of m being 1.

5. A polymer comprising as constituent units monomer units represented by the formula [1a]:

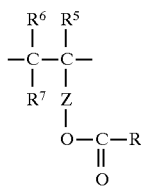    [1a]

wherein $R^5$, $R^6$ and $R^7$ are independently a hydrogen atom, an alkyl group, a cyano group, an alkyloxycarbonyl group or a carbamoyl group; Z is a spacer or a direct link; and R is a hydroxyalkyl group having a protected terminal hydroxyl group.

6. A polymer according to claim 5, wherein in the formula [1a], the hydroxyalkyl group having a protected terminal hydroxyl group which is represented by R is a group represented by the formula [2]:

    [2]

wherein $R^1$ and $R^2$ are independently a hydrogen atom, a substituted or unsubstituted alkyl group or an alicyclic hydrocarbon group, and $R^1$ and $R^2$ may form together an aliphatic ring; and $R^3$ is an alkyl group, an alkenyl group, a hydroxyalkyl group, an alkyloxycarbonyl group or an alkylsilyl group, or the formula [3]:

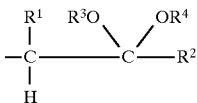    [3]

wherein $R^4$ is an alkyl group; and $R^1$, $R^2$ and $R^3$ are as defined above, and $R^3$ and $R^4$ may form together an aliphatic ring.

7. A polymer according to claim 5, wherein the spacer is a group represented by the formula [4]:

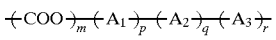    [4]

wherein $A_2$ is a divalent hydrocarbon group which may have one or more oxygen atoms; $A_1$ and $A_3$ are independently a lower alkylene group; m is 0 or 1; and p, q and r are independently 0 or 1, provided that q is 1 in the case of m being 1.

8. A polymer according to claim 5, wherein in the formula [1a], the hydroxyalkyl group having a protected terminal hydroxyl group which is represented by R is a group represented by the formula [2]:

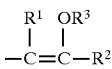    [2]

wherein $R^1$ and $R^2$ are independently a hydrogen atom, a substituted or unsubstituted alkyl group or an alicyclic hydrocarbon group, and $R^1$ and $R^2$ may form together an aliphatic ring; and $R^3$ is an alkyl group, an alkenyl group, a hydroxyalkyl group, an alkyloxycarbonyl group or an alkylsilyl group, or the formula [3]:

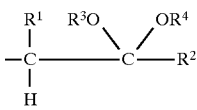    [3]

wherein $R^4$ is an alkyl group; and $R^1$, $R^2$ and $R^3$ are as defined above, and $R^3$ and $R^4$ may form together an aliphatic ring, and the spacer is a group represented by the formula [4]:

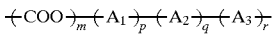    [4]

wherein $A_2$ is a divalent hydrocarbon group which may have one or more oxygen atoms; $A_1$ and $A_3$ are independently a lower alkylene group; m is 0 or 1; and p, q and r are independently 0 or 1, provided that q is 1 in the case of m being 1.

9. A polymer according to claim 5, which is a homopolymer comprising monomer units of the formula [1a] as constituent units.

10. A polymer according to claim 5, which is a copolymer comprising two or more kinds of monomer units of the formula [1a] as constituent units.

11. A polymer according to claim 5, which is a copolymer comprising as constituent units one or more kinds of monomer units of the formula [1a] and one or more kinds of monomer units of the formula [1b]:

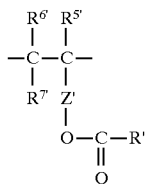 [1b]

wherein $R^{5'}$, $R^{6'}$, $R^{7'}$ are independently a hydrogen atom, an alkyl group, a cyano group, an alkyloxycarbonyl group or a carbamoyl group; Z' is a spacer or a direct link; and R' is a hydroxyalkyl group.

12. A polymer according to claim 5, which is a copolymer comprising as constituent units one or more kinds of monomer units of the formula [1a] and one or more kinds of monomer units of the formula [6a]:

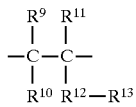 [6a]

wherein $R^9$ is a hydrogen atom, a lower alkyl group or a halogen atom; $R^{10}$ is a hydrogen atom, a lower alkyl group, a halogen atom, a carboxyl group, an alkyloxycarbonyl group or a formyl group; $R^{11}$ is a hydrogen atom, a lower alkyl group, a carboxyl group, an alkyloxycarbonyl group or a halogen atom; $R^{12}$ is an alkylene group which may have a double bond, or a direct link; and $R^{13}$ is a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, an aryloxycarbonyl group, an acyloxy group, a cyano group, a carboxyl group, a formyl group, an amino group, a sulfonic acid group, a carbamoyl group or a hydroxyl group, and $R^{10}$ and $R^{13}$ may form together a group of the formula:
—CO—O—CO— or —CO—NH—CO—.

13. A monomer according to claim 1, wherein the monomer represented by the formula [1] is a monomer represented by the formula [1]-1:

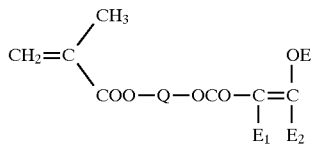 [1]-1 wherein Q is a divalent hydrocarbon group which may have one or more oxygen atoms; E is a lower alkyl group; and $E_1$ and $E_2$ are independently a hydrogen atom, and $E_1$ and $E_2$ may form together an aliphatic ring, or the formula [1]-2:

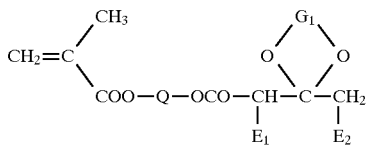 [1]-2 wherein Q is a divalent hydrocarbon group which may have one or more oxygen atoms; $G_1$ is a lower alkylene group; and $E_1$ and $E_2$ are independently a hydrogen atom, and $E_1$ and $E_2$ may form together an aliphatic ring.

14. A monomer according to claim 1, wherein the monomer represented by the formula [1] is a monomer represented by the formula [1]-3:

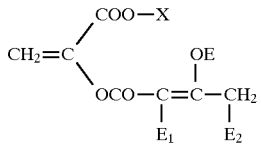 [1]-3 wherein X is an alkyl group; E is a lower alkyl group; and $E_1$ and $E_2$ are independently a hydrogen atom, and $E_1$ and $E_2$ may form together an aliphatic ring, or the formula [1]-4:

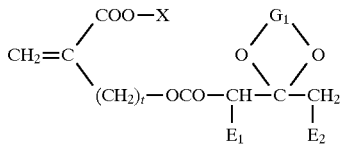 [1]-4 wherein X is an alkyl group; $G_1$ is a lower alkylene group; t is an integer of 0 to 6; and $E_1$ and $E_2$ are independently a hydrogen atom, and $E_1$ and $E_2$ may form together an aliphatic ring.

* * * * *